United States Patent

Masaki et al.

[11] Patent Number: 5,773,437
[45] Date of Patent: Jun. 30, 1998

[54] ALKYLENEDIAMINE DERIVATIVES

[75] Inventors: Mitsuo Masaki, Chiba; Norihisa Miyake, Saitama; Atsushi Tendo, Saitama; Michiko Ishida, Saitama; Haruhiko Shinozaki, Saitama; Yutaka Nomura, Chiba; Yasunori Goto, Tokyo, all of Japan

[73] Assignee: Nippon Chemiphar Co., Ltd., Tokyo, Japan

[21] Appl. No.: 722,112

[22] PCT Filed: Mar. 31, 1995

[86] PCT No.: PCT/JP95/00632

§ 371 Date: Sep. 30, 1996

§ 102(e) Date: Sep. 30, 1996

[87] PCT Pub. No.: WO95/26959

PCT Pub. Date: Oct. 12, 1995

[30] Foreign Application Priority Data

Mar. 31, 1994 [JP] Japan ................................. 6-085831
Apr. 18, 1994 [JP] Japan ................................. 6-103345

[51] Int. Cl.$^6$ ..................... A61K 31/54; C07D 279/02

[52] U.S. Cl. ................................ 514/224.2; 514/226.5; 544/49; 544/50

[58] Field of Search ............... 544/49, 50; 514/224.2, 514/226.5

[56] References Cited

U.S. PATENT DOCUMENTS

| 3,712,889 | 1/1973 | Sianesi et al. | 260/243 |
|---|---|---|---|
| 4,272,531 | 6/1981 | DeMarinis | 424/246 |
| 5,037,841 | 8/1991 | Schohe et al. | 514/373 |
| 5,274,097 | 12/1993 | Schohe et al. | 546/208 |

OTHER PUBLICATIONS

Orazi et al., J. Het. Chem., 23, 1701–8, Nov. 1986.
Sianesi et al., J. Med. Chem., 16(10), 1133–37, 1973.

*Primary Examiner*—Johann Richter
*Assistant Examiner*—Laura Cross Lutz
*Attorney, Agent, or Firm*—McAulay Fisher Nissen Goldberg & Kiel, LLP

[57] ABSTRACT

The present invention relates to alkylenediamine derivatives which relieve urinating contraction and therefore are of value as active ingredients of therapeutic agents for treating dysuria.

4 Claims, No Drawings

ALKYLENEDIAMINE DERIVATIVES

This is a 371 of PCT/JP95/00632 filed Mar. 31, 1995.

FIELD OF THE INVENTION

The present invention relates to a novel alkylenediamine derivative which shows a function to relieve urinating contraction and therefore is of value as an active ingredient of a therapeutic agent for treating dysuria.

BACKGROUND OF THE INVENTION

Heretofore, flavoxate hydrochloride and oxybutynin hydrochloride which directly function peripherally on urinary bladder have been used as therapeutic agents for treating dysuria. However, these compounds may give certain side-effects to other organs such as digestive apparatus.

EP-0579169-A1 (Japanese Patent Provisional Publication H6-80645) describes an alkylenediamine of the formula (A):

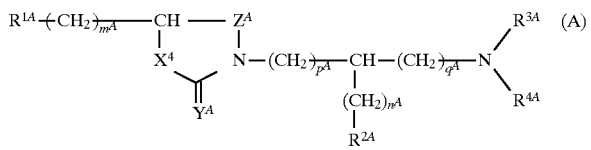

in which each of $R^{1A}$ and $R^{2A}$ independently represents a phenyl, naphthyl or aromatic heterocyclic group which may have one to five same or different substituents selected from the group consisting of alkyl, halogen, haloalkyl, hydroxyl, alkoxy, aryloxy, aralkyloxy, nitro, amino, alkylamino, aralkylamino, arylamino, acylamino, carboxyl, alkoxycarbonyl, aralkyloxycarbonyl, aryloxycarbonyl, amide, sulfo, alkoxysulfonyl, aralkyloxysulfonyl, aryloxysulfonyl, sulfonamide, and 1H-tetrazol-5-yl; each of $R^{3A}$ and $R^{4A}$ independently represents hydrogen, alkyl, aralkyl or aryl, otherwise $R^{3A}$ and $R^{4A}$ are combined in conjunction with the nitrogen atom to which $R^{3A}$ and $R^{4A}$ are attached to form 5 to 7 membered ring which may contain oxygen, sulfur or nitrogen and which may have a substituent selected from the group consisting of alkyl, aralkyl, phenyl, hydroxyl, alkoxy, carboxyl, alkoxycarbonyl, aralkyloxycarbonyl, aryloxycarbonyl, and amide; $X^A$ represents oxygen, sulfur or imino; A represents oxygen or sulfur; $Z^A$ represents —$CH_2$—, —CO—, or —CS—; $m^A$ is an integer of 0 to 4; $n^A$ is an integer of 0 to 4; each of $p^A$ and $q^A$ independently is an integer of 0 to 5 under the condition that the total of $p^A$ and $q^A$ is in the range of 1 to 5, or its pharmacologically acceptable salt is of value as an active ingredient of a therapeutic agent for treating dysuria, because the compound can relieve urinating contraction which is observed under high intracystic pressure, and therefore is employable for treating nervous dysuria, chronic prostatitis, chronic cystitis, dysuria caused by neurogenic bladder or unstable bladder, incontinence of urine, urgency of micturition, and residual urine.

The object of the invention is to provide a novel alkylenediamine derivative showing a function to relieve urinating contraction which is observed under high intracystic pressure.

DISCLOSURE OF THE INVENTION

The present invention resides in an alkylenediamine derivative of benzothiazine type which is represented by the formula (1):

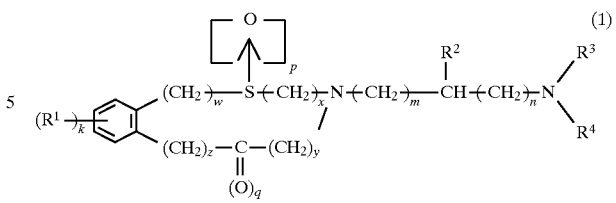

in which $R^1$ represents an atom or a group selected from the group consisting of hydrogen, alkyl having 1–8 carbon atoms, halogen, haloalkyl having 1–4 carbon atoms, hydroxyl, alkoxy having 1–8 carbon atoms, aryloxy having 4–10 carbon atoms, aralkyloxy having 5–14 carbon atoms (its alkyl portion has 1–4 carbon atoms), nitro, amino, cyano, alkylamino having 1–8 carbon atoms, aralkylamino having 5–14 carbon atoms (its alkyl portion has 1–4 carbon atoms), arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms (its alkyl portion has 1–4 carbon atoms), aryloxycarbonyl having 5–11 carbon atoms, carbamoyl, sulfo, alkoxysulfonyl having 1–8 carbon atoms, aralkyloxysulfonyl having 5–14 carbon atoms (its alkyl portion has 1–4 carbon atoms), aryloxysulfonyl having 4–10 carbon atoms, sulfonamide, and 1H-tetrazol-5-yl;

$R^2$ represents hydrogen, hydroxyl, alkyl having 1–8 carbon atoms, alkenyl having 2–9 carbon atoms, alkoxy having 1–8 carbon atoms, or an aryl having 4–10 carbon atoms, aralkyl having 5–14 carbon atoms (its alkyl portion has 1–4 carbon atoms) or aromatic heterocyclic group which may have one to five same or different substituents selected from the group consisting of alkyl having 1–8 carbon atoms, halogen, haloalkyl having 1–4 carbon atoms, hydroxyl, alkoxy having 1–8 carbon atoms, aryloxy having 4–10 carbon atoms, aralkyloxy having 5–14 carbon atoms (its alkyl portion has 1–4 carbon atoms), nitro, amino, cyano, alkylamino having 1–8 carbon atoms, aralkylamino having 5–14 carbon atoms (its alkyl portion has 1–4 carbon atoms), arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms (its alkyl portion has 1–4 carbon atoms), aryloxycarbonyl having 5–11 carbon atoms, carbamoyl, sulfo, alkoxysulfonyl having 1–8 carbon atoms, aralkyloxysulfonyl having 5–14 carbon atoms (its alkyl portion has 1–4 carbon atoms), aryloxysulfonyl having 4–10 carbon atoms, sulfonamide and 1H-tetrazol-5-yl;

each of $R^3$ and $R^4$ independently represents hydrogen, alkyl having 1–8 carbon atoms, aralkyl having 5–14 carbon atoms (its alkyl portion has 1–4 carbon atoms), or aryl having 4–10 carbon atoms, or $R^3$ and $R^4$ form in combination with the nitrogen atom to which $R^3$ and $R^4$ are attached, a hetero ring which may contain another nitrogen, oxygen or sulfur as the ring-forming atom in addition to the former nitrogen atom;

k is an integer of 1 to 4;

each of m and n independently represents an integer of 0 to 4, under the condition that the total number of m and n is in the range of 0 to 4;

p is 0, 1 or 2;

q is 0 or 1; and each of w, x, y and z independently is an integer of 0 to 2, under the condition that the total number of w, x, y and z is 1 or 2.

Among the alkylenediamine derivatives of benzothiazine type represented by the above-mentioned formula (1), preferred is an alkylenediamine derivative having the following formula (2):

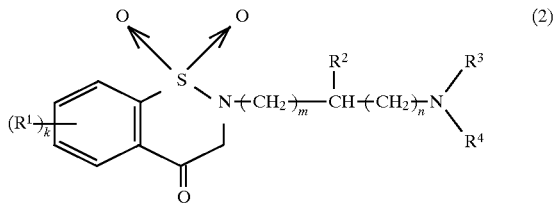

in which $R^1$, $R^2$, $R^3$, $R^4$, k, m, and n are the same as those defined for the formula (1).

Among the alkylenediamine derivatives of benzothiazine type represented by the above-mentioned formula (1), also preferred is an alkylenediamine derivative having the following formula (3):

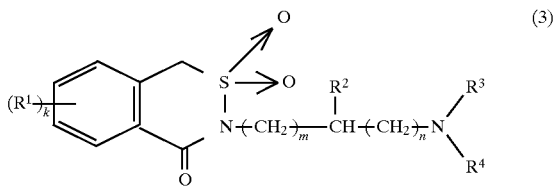

in which $R^1$, $R^2$, $R^3$, $R^4$, k, m, and n are the same as those defined for the formula (1).

The alkylenediamine derivative of the formula (1) entirely differs from the alkylenediamine derivative of the aforementioned EP-0579169-A1 in that the former has on one end a condensed heterocyclic ring containing sulfur and nitrogen atoms.

The present invention further provides an alkylenediamine derivative of saccharin type having the formula (I):

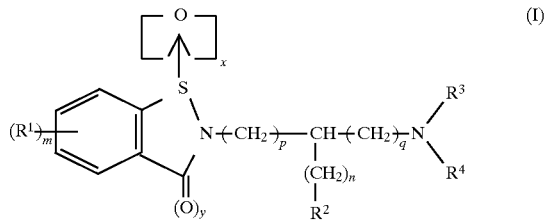

in which $R^1$ represents an atom or a group selected from the group consisting of hydrogen, alkyl having 1–8 carbon atoms, halogen, haloalkyl having 1–4 carbon atoms, hydroxyl, alkoxy having 1–8 carbon atoms, aryloxy having 4–10 carbon atoms, aralkyloxy having 5–14 carbon atoms (its alkyl portion has 1–4 carbon atoms), nitro, amino, cyano, alkylamino having 1–8 carbon atoms, aralkylamino having 5–14 carbon atoms (its alkyl portion has 1–4 carbon atoms), arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms (its alkyl portion has 1–4 carbon atoms), aryloxycarbonyl having 5–11 carbon atoms, carbamoyl, sulfo, alkoxysulfonyl having 1–8 carbon atoms, aralkyloxysulfonyl having 5–14 carbon atoms (its alkyl portion has 1–4 carbon atoms), aryloxysulfonyl having 4–10 carbon atoms, sulfonamide, and 1H-tetrazol-5-yl;

$R^2$ represents phenyl, naphthyl or aromatic heterocyclic group which may have one to five same or different substituents selected from the group consisting of alkyl having 1–8 carbon atoms, halogen, haloalkyl having 1–4 carbon atoms, hydroxyl, alkoxy having 1–8 carbon atoms, aryloxy having 4–10 carbon atoms, aralkyloxy having 5–14 carbon atoms (its alkyl portion has 1–4 carbon atoms), nitro, amino, cyano, alkylamino having 1–8 carbon atoms, aralkylamino having 5–14 carbon atoms (its alkyl portion has 1–4 carbon atoms), arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms (its alkyl portion has 1–4 carbon atoms), aryloxycarbonyl having 5–11 carbon atoms, carbamoyl, sulfo, alkoxysulfonyl having 1–8 carbon atoms, aralkyloxysulfonyl having 5–14 carbon atoms (its alkyl portion has 1–4 carbon atoms), aryloxysulfonyl having 4–10 carbon atoms, sulfonamide and 1H-tetrazol-5-yl;

each of $R^3$ and $R^4$ independently represents hydrogen, alkyl having 1–8 carbon atoms, aralkyl having 5–14 carbon atoms (its alkyl portion has 1–4 carbon atoms), or aryl having 4–10 carbon atoms, or $R^3$ and $R^4$ form in combination with the nitrogen atom to which $R^3$ and $R^4$ are attached, a five to seven membered hetero ring having the formula (II):

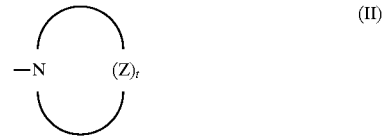

in which Z is a group of the formula (III):

in which $R^5$ represents hydrogen or a group selected from the group consisting of alkyl having 1–8 carbon atoms, aralkyl having 5–14 carbon atoms (its alkyl portion has 1–4 carbon atoms), phenyl, 2-pyrimidinyl, carboxyl, alkoxycarbonyl having 2–9 carbon atoms, aralkyl-oxycarbonyl having 6–15 carbon atoms (its alkyl portion has 1–4 carbon atoms), and aryloxycarbonyl having 5–11 carbon atoms, —O—, —S—, —SO—, or —SO$_2$—, and t is 0 or 1;

in which the five to seven hetero ring may have 1 to 5 substituents selected from the group consisting of alkyl having 1–5 carbon atoms, aralkyl having 5–14 carbon atoms (its alkyl has 1–4 carbon atoms), phenyl, hydroxyl, alkoxy having 1–8 carbon atoms, carboxyl, alkoxycarbonyl having 2–9 carbon atoms, aralkyloxycarbonyl having 6–15 carbon atoms (its alkyl has 1–4 carbon atoms), aryloxycarbonyl having 5–11 carbon atoms, aliphatic acyl having 1–8 carbon atoms, aromatic acyl having 5–11 carbon atoms, and carbamoyl;

m represents an integer of 1 to 4, and n represents an integer of 0 to 4;

each of p and q independently represents an integer of 0 to 5, under the condition that the total number of p and q is in the range of 1 to 5;

x is 0, 1 or 2; and y is 0 or 1.

Among the alkylenediamine derivatives of saccharin type represented by the above-mentioned formula (I), preferred is an alkylenediamine derivative having the following formula (IV):

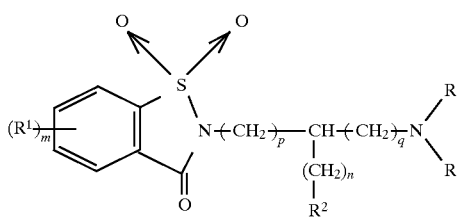

in which $R^1$, $R^2$, $R^3$, $R^4$, m, n, p and q are the same as those defined for the formula (I).

Among the alkylenediamine derivatives of saccharin type represented by the above-mentioned formula (I), also preferred is an alkylenediamine derivative having the following formula (V):

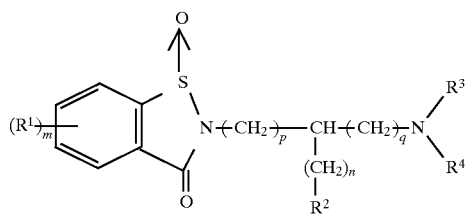

in which $R^1$, $R^2$, $R^3$, $R^4$, m, n, p and q are the same as those defined for the formula (I).

Among the alkylenediamine derivatives of saccharin type represented by the above-mentioned formula (I), also preferred is an alkylenediamine derivative having the following formula (VI):

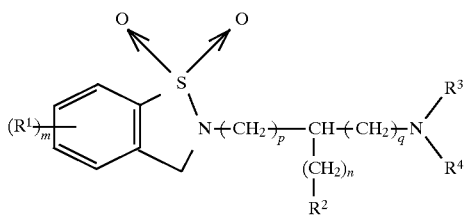

in which $R^1$, $R^2$, $R^3$, $R^4$ m, n, p and q are the same as those defined for the formula (I).

The alkylenediamine derivative of the formula (I) entirely differs from the alkylenediamine derivative of the aforementioned EP-0579169-A1 in that the former has on one end a benzisothiazoline structure.

PREFERRED EMBODIMENTS OF THE INVENTION

In the formula (1), the halogen represented by $R^1$ preferably is fluorine, chlorine or bromine, and chlorine is most preferred. The alkyl having 1–8 carbon atoms which is represented by $R^1$ preferably is methyl, ethyl, propyl, isopropyl, butyl, isobutyl, pentyl, hexyl, heptyl, or octyl. The haloalkyl having 1–4 carbon atoms preferably is trifluoromethyl, chloromethyl, or fluoromethyl. The alkoxy having 1–8 carbon atoms preferably is methoxy, ethoxy, or propoxy. The aryloxy having 4–10 carbon atoms (which may have nucleus substituents such as halogen, cyano, alkyl, alkoxy, amino, or alkoxycarbonyl) preferably is phenoxy or p-chlorophenoxy. The aralkyloxy having 5–14 carbon atoms (its alkyl portion has 1–4 carbon atoms) preferably is benzyloxy, pyridylmethyloxy, naphthylmethyloxy, or thenyloxy. The alkylamino having 1–8 carbon atoms preferably methylamino, dimethylamino, ethylamino, propylamino, or isobutylamino. The aralkylamino having 5–14 carbon atoms (its alkyl portion has 1–4 carbon atoms, and which may have nucleus substituents such as halogen, cyano, alkyl, alkoxy, amino, or alkoxycarbonyl) preferably is benzylamino or (4-chlorophenyl)methylamino. The arylamino having 4–10 carbon atoms (which may have nucleus substituents such as halogen, cyano, alkyl, alkoxy, amino, or alkoxycarbonyl) preferably is phenylamino or p-chlorophenylamino. The aliphatic acylamino having 1–8 carbon atom preferably is acetylamino or propionylamino. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, naphthyloxycarbonyl, or thienyloxycarbonyl. The alkoxysulfonyl having 1–8 carbon atoms preferably is methoxysulfonyl or ethoxysulfonyl. The aralkyloxysulfonyl having 5–14 carbon atoms (its alkyl portion has 1–4 carbon atoms) preferably is benzyloxysulfonyl, naphthylmethyloxysulfonyl, or thenyloxysulfonyl. The aryloxysulfonyl having 4–10 carbon atoms preferably is phenoxysulfonyl, naphthyloxysulfonyl, or thienyloxysulfonyl.

In the formula (1), particularly preferred for $R^1$ is hydrogen, halogen, alkyl having 1–8 carbon atoms, or alkoxy having 1–8 carbon atoms.

In the formula (1), $R^2$ represents hydrogen, hydroxyl, alkyl having 1–8 carbon atoms, alkenyl having 2–9 carbon atoms, alkoxy having 1–8 carbon atoms, or aryl having 4–10 carbon atoms, aralkyl having 5–14 carbon atoms (its alkyl portion has 1–4 carbon atoms), or aromatic heterocyclic group which may have one to five same or different substituents. The alkyl having 1–8 carbon atoms which is represented by $R^2$ preferably is methyl, ethyl, propyl, isopropyl, butyl, isobutyl, pentyl, hexyl, heptyl, or octyl. The alkenyl having 2–9 carbon atoms preferably is allyl, 1-propenyl, 2-methyl-2-propenyl, 2-methyl-1-propenyl, 1-butenyl, 2-butenyl, 3-butenyl, 3-methyl-3-butenyl, 3-methyl-2-butenyl, 4-pentenyl, 4-methyl-4-pentenyl, 4-methyl-3-pentenyl, 5-hexenyl, 5-methyl-5-hexenyl, 5-methyl-4-hexenyl, 6-heptenyl, 6-methyl-6-heptenyl, 6-methyl-5-heptenyl, 7-octenyl, 7-methyl-7-octenyl, or 7-methyl-6-octenyl. The alkoxy having 1–8 carbon atoms preferably is methoxy, ethoxy, or propoxy. The aryl having 4–10 carbon atoms preferably is phenyl or naphthyl. The aralkyl having 5–14 carbon atoms (its alkyl portion has 1–4 carbon atoms) preferably is benzyl or naphthylmethyl. The aromatic hetero ring preferably is furan ring, thiophene ring, pyridine ring, quinoline ring, or indole ring.

The halogen which may be attached to the above-mentioned aryl, aralkyl or aromatic heterocyclic group preferably is fluorine, chlorine, or bromine. The alkyl having 1–8 carbon atoms preferably is methyl, ethyl, propyl, isopropyl, butyl, isobutyl, pentyl, hexyl, heptyl, or octyl. The haloalkyl having 1–4 carbon atoms preferably is trifluoromethyl, chloromethyl, or fluoromethyl. The alkoxy having 1–8 carbon atoms preferably is methoxy, ethoxy, or propoxy. The aryloxy having 4–10 carbon atoms (which may have nucleus substituents such as halogen, cyano, alkyl, alkoxy, amino, or alkoxycarbonyl) preferably is phenoxy or p-chlorophenoxy. The aralkyloxy having 5–14 carbon atoms (its alkyl portion has 1–4 carbon atoms) preferably is benzyloxy, pyridylmethyloxy, naphthylmethyloxy, or thenyloxy. The alkylamino having 1–8 carbon atoms preferably is methylamino, dimethylamino, ethylamino, propylamino, or isobutylamino. The aralkylamino having 5–14 carbon atoms (its alkyl portion has 1–4 carbon atoms, and which may have nucleus substituents such as halogen, cyano, alkyl, alkoxy, amino, or alkoxycarbonyl) preferably is benzylamino or (4-chlorophenyl)methylamino. The arylamino having 4–10 carbon atoms (which may have nucleus substituents such as halogen, cyano, alkyl, alkoxy, amino, or alkoxycarbonyl) preferably is phenylamino or p-chlorophenylamino. The aliphatic acylamino having 1–8 carbon atom preferably is acetylamino or propionylamino. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, pyridyloxycarbonyl, naphthyloxycarbonyl, or thienyloxycarbonyl. The alkoxysulfonyl having 1–8 carbon atoms preferably is methoxysulfonyl or ethoxysulfonyl. The aralkyloxysulfonyl having 5–14 carbon atoms (its alkyl portion has 1–4 carbon atoms) preferably is benzyloxysulfonyl, naphthylmethyloxysulfonyl, or thenyloxysulfonyl. The aryloxysulfonyl having 4–10 carbon atoms preferably is phenoxysulfonyl, naphthyloxysulfonyl, or thienyloxysulfonyl.

Particularly preferred for $R^2$ is hydrogen, alkyl having 1–8 carbon atoms, alkoxy having 1–8 carbon atoms, hydroxyl, or phenyl, furyl, thienyl or pyridyl which has no substituents, or phenyl having, as substituent, halogen, alkyl having 1–8 carbon atoms, or alkoxy having 1–8 carbon atoms.

In the formula (1), the alkyl having 1–8 carbon atoms which is represented by $R^3$ or $R^4$ preferably is methyl, ethyl, propyl, isopropyl, butyl, or isobutyl. The aralkyl having 5–14 carbon atoms (its alkyl portion has 1–4 carbon atoms) preferably is benzyl, phenylethyl, or phenylpropyl. The aryl having 4–10 carbon atoms preferably is phenyl, pyridyl, or naphthyl.

The heterocyclic group which is formed by the combination of $R^3$ and $R^4$ and the nitrogen atom to which $R^3$ and $R^4$ are attached and which may further have nitrogen, oxygen, or sulfur as the ring member preferably is a five to seven membered heterocyclic group having the formula (4):

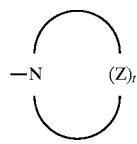  (4)

in which Z is a group of the formula (5):

  (5)

[in which $R^5$ represents hydrogen, or a group selected from the group consisting of alkyl having 1–8 carbon atoms, aralkyl having 5–14 carbon atoms (its alkyl portion has 1–4 carbon atoms), phenyl, 2-pyrimidinyl, carboxyl, alkoxycarbonyl having 2–9 carbon atoms, aralkyloxycarbonyl having 6–15 carbon atoms (its alkyl portion has 1–4 carbon atoms), and aryloxycarbonyl having 5–11 carbon atoms], —O—, —S—, —SO—, or —SO$_2$—, and t is 0 or 1, or 1,2,3,4-tetrahydroisoquinoline group, or 2,3-dihydro-1H-benz[de]isoquinoline group.

The five to seven membered heterocyclic group represented by the formula (4) preferably is morpholino, piperidino, homomorpholino, 1-pyrrolidinyl, thiomorpholino, 1-piperazinyl, perhydroazepin-1-yl, S-oxythiomorpholino, or S,S-dioxythiomorpholino.

The alkyl having 1–8 carbon atoms which is represented by $R^5$ of the formula (5) for Z of the formula (4) preferably is methyl, ethyl, propyl, isopropyl, butyl, or isobutyl. The aralkyl having 5–14 carbon atoms (its alkyl has 1–4 carbon atoms) preferably is benzyl, phenylethyl, or phenylpropyl. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, naphthyloxycarbonyl, or thienyloxycarbonyl.

The five to seven membered heterocyclic group of the formula (4), 1,2,3,4-tetrahydroisoquinoline group, or 2,3-dihydro-1H-benz[de]isoquinoline group may have 1 to 5 substituents selected from the group consisting of alkyl having 1–8 carbon atoms which may have one or two substituents such as aryl having 4–10 carbon atoms (which may be substituted with halogen, alkyl having 1–5 carbon atoms, alkoxy having 1–5 carbon atoms, or aliphatic acyl having 1–5 carbon atoms), phenyl, hydroxyl, alkoxy having 1–8 carbon atoms which may have one or two substituents such as aryl having 4–10 carbon atoms (which may be substituted with halogen, alkyl having 1–5 carbon atoms, alkoxy having 1–5 carbon atoms, or aliphatic acyl having 1–5 carbon atoms), aryloxy having 4–10 carbon atoms, aralkylthio having 5–14 carbon atoms (its alkyl portion has 1–4 carbon atoms), arylthio having 4–10 carbon atoms, carboxyl, alkoxycarbonyl having 2–9 carbon atoms, aralkyloxycarbonyl having 6–15 carbon atoms (its alkyl portion has 1–4 carbon atoms), aryloxycarbonyl having 5–11 carbon atoms, aliphatic acyl having 1–8 carbon atoms, aromatic acyl having 5–11 carbon atoms, cyano, and carbamoyl.

Among the above-mentioned substituents, the alkyl having 1–5 carbon atoms preferably is methyl, ethyl, propyl, isopropyl, butyl, or isobutyl. The alkyl having 1–8 carbon atoms which may have one or two substituted or unsubstituted aryl having 4–10 carbon atoms preferably is benzyl, phenylethyl, phenylpropyl, diphenylmethyl, chlorobenzyl, methylbenzyl, methoxybenzyl, acetylbenzyl, or thienylmethyl. The alkoxy having 1–8 carbon atoms which may have one or two substituted or unsubstituted aryl having 4–10 carbon atoms preferably is methoxy, ethoxy, propoxy, benzyloxy, diphenylmethyloxy, phenylethyloxy, chlorobenzyloxy, methylbenzyloxy, methoxybenzyloxy, acetylbenzyloxy, 2-thienylmethyloxy, naphthylmethyloxy, 2-pyridylmethyloxy, chloronaphthylmethyloxy, dichlorobenzyloxy, or di(chlorophenyl)methyloxy. The aryloxy having 4–10 carbon atoms preferably is phenoxy, chlorophenoxy, 3-thienyloxy, methoxyphenoxy, methylphenoxy, acetylphenoxy, dichlorophenoxy, naphthyloxy, chloronaphthyloxy, or 4-pyridyloxy. The aralkylthio having 5–14 carbon atoms (its alkyl portion has 1–4 carbon atoms) preferably is benzylthio, phenylethylthio, chlorobenzylthio, methylbenzylthio, methoxybenzylthio, acetylbenzylthio, 2-thienylmethylthio, naphthylmethylthio, 2-pyridylmethylthio, chloronaphthylmethylthio, dichlorobenzylthio, or di(chlorophenyl)methylthio. The arylthio having 4–10 carbon atoms preferably is phenylthio, 3-thienylthio, methoxyphenylthio, methylphenylthio, acetylphenylthio, dichlorophenylthio, naphthylthio, chloronaphthylthio, or 4-pyridylthio. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, naphthyloxycarbonyl, or thienyloxycarbonyl. The aliphatic acyl having 1–8 carbon atoms preferably is formyl, acetyl, or propionyl. The aromatic acyl having 5–11 carbon atoms preferably is benzoyl or phthaloyl. If the two or more substituents are attached, these substituents may be the same or different.

The five to seven membered heterocyclic group represented by the formula (4) preferably is morpholino, piperidino, homomorpholino, 1-pyrrolidinyl, thiomorpholino, 1-piperazinyl, perhydroazepin-1-yl, S-oxythiomorpholino, or S,S-dioxythiomorpholino. The heterocyclic group may not have substituents, or may have substituents such as alkyl having 1–8 carbon atoms, alkyl having 1–8 carbon atoms which have one or two phenyl groups, phenyl, thienyl, acyl having 1–8 carbon atoms, carbamoyl, or 2-pyrimidinyl on its carbon or nitrogen atom.

In the formula (1), k preferably is 1 or 2, and 1 is most preferred. m preferably is 0. n preferably is 1, 2, or 3. The alkylenediamine derivative of the formula (1) in which p, q, w, x, y and z are 2, 1, 0, 0, 1 and 0, respectively, corresponds to the alkylenediamine derivative of the formula (2). The alkylenediamine derivative of the formula (1) in which p, q, w, x, y and z are 2, 1, 1, 1, 0, 0 and 0, respectively, corresponds to the alkylenediamine derivative of the formula (3). In the formula (1), if q is o, two hydrogen atoms are attached.

The alkylenediamine derivative derivative of the formula (1) can be synthesized utilizing reactions which are known in the technical field of organic chemistry.

For instance, the alkylenediamine of the formula (2) can be prepared by reacting a ketal compound having the formula (6):

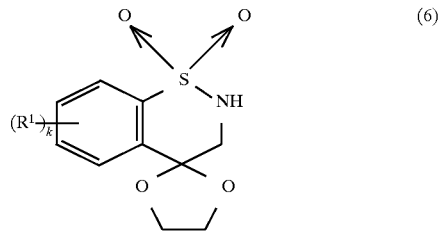

in which $R^1$ and k have the same meanings as defined in the formula (1)
with a compound having the formula (7):

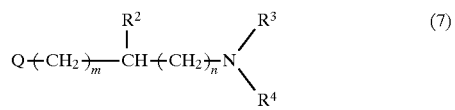

in which $R^2$, $R^3$, $R^4$, m and n have the same meanings as defined in the formula (1), and Q is a releasable group such as halogen, tosyloxy, or mesyloxy, to give an ethylene ketal compound, and then subjecting the resulting compound to de-ketal reaction.

In the above-mentioned preparation process, the ketal compound of the formula (6) and the compound of the formula (7) are caused to react at a temperature from room temperature to the reflux temperature for 1 to 50 hours, in an organic solvent such as acetone, dimethylformamide, methyl ethyl ketone, isobutyl methyl ketone, isopropyl alcohol, ethanol, or dimethoxyethane, in the presence of a base such as potassium carbonate, sodium carbonate, cesium carbonate, sodium hydrogen carbonate, sodium hydride, sodium metal, sodium ethoxide, or sodium hydroxide, to prepare an ethylene ketal compound corresponding to the compound of the formula (2). In the reaction, 1 to 2 moles of the compound of the formula (7) and the 2 to 8 moles of the base are preferably employed per one mole of the compound of the formula (6). Subsequently, the ethylene ketal is subjected to the reaction for removing the ketal by treating with diluted hydrochloric acid, diluted hydrochloric acid/methanol mixture, diluted hydrochloric acid/tetrahydrofuran mixture, diluted hydrochloric acid/ethnaol mixture, sulfuric acid/acetone mixture, p-toluenesulfonic acid/acetone mixture, 80% acetic acid, silica gel/water/dichloromethane mixture, oxalic acid/water/dichloromethane mixture, sulfuric acid/water/dichloromethane mixture, or triphenylmethyl tetrafluoroborate/dichloromethane mixture, to give the alkylenediamine derivative of the formula (2).

Alternatively, the alkylenediamine derivative of the formula (2) can be prepared by reacting a ketal compound of the formula (8):

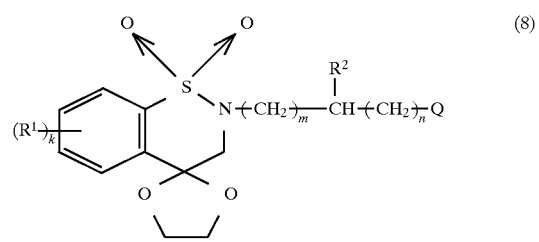

in which $R^1$, $R^2$, k, m and n have the same meanings as defined in the formula (1), and Q is a releasable group such as halogen, tosyloxy, or mesyloxy, with a compound having the formula (9):

in which $R^3$ and $R^4$ have the same meanings as defined in the formula (1), to give an ethylene ketal compound, and then subjecting the resulting compound to de-ketal reaction.

In the above-mentioned preparation process, the ketal compound of the formula (8) and the compound of the formula (9) are caused to react at 50° to 150° C. for 1 to 2 hours, generally, in the absence of a solvent, to give an ethylene ketal compound which corresponds to the compound of the formula (2). The ethylene ketal compound is then subjected to a reaction for removal of ketal structure in the same manner as above, to give the alkylenediamine derivative of the formula (2).

In the reaction, 1 to 2 moles of the compound of the formula (9) is preferably employed per one mole of the compound of the formula (8).

A compound of the formula (1) in which p is 0 or 1, or q is 0, which is similar to the compound of the formula (2) can be synthesized in a manner similar to the above-mentioned process.

The alkylenediamine derivative of the formula (3) can be prepared by reacting a compound of the formula (10):

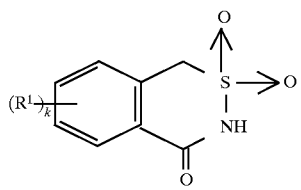

in which $R^1$ and k have the same meanings as defined in the formula (1) with a compound of the aformementioned formula (7).

In the above-mentioned preparation process, the compound of the formula (10) and the compound of the formula (7) are caused to react at a temperature from room temperature to the reflux temperature for 1 to 50 hours, in an organic solvent such as acetone, dimethylformamide, methyl ethyl ketone, isobutyl methyl ketone, isopropyl alcohol, ethanol, or dimethoxyethane, in the presence of a base such as potassium carbonate, sodium carbonate, cesium carbonate, sodium hydrogen carbonate, sodium hydride, metallic sodium, sodium ethoxide, or sodium hydroxide, to prepare an ethylene ketal compound corresponding to the compound of the formula (3). In the reaction, 1 to 2 moles of the compound of the formula (7) and the 2 to 8 moles of the base are preferably employed per one mole of the compound of the formula (10).

Alternatively, the alkylenediamine derivative of the formula (3) can be prepared by reacting a compound of the formula (11):

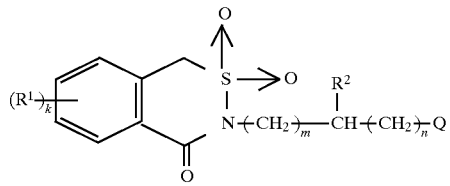

in which $R^1$, $R^2$, k, m and n have the same meanings as defined in the formula (1), and Q is a releasable group as mentioned above, with a compound having the aforementioned formula (9).

In the above-mentioned preparation process, the compound of the formula (11) and the compound of the formula (9) are caused to react at 50° to 150° C. for 1 to 20 hours, generally, in the absence of a solvent, to give the compound of the formula (3). If necessary, a solvent which does not participate in the reaction can be employed.

A compound of the formula (1) in which p is 0 or 1, or q is 0, which is similar to the compound of the formula (3) can be synthesized in a manner similar to the above-mentioned process.

Further, a compound having the formula (12):

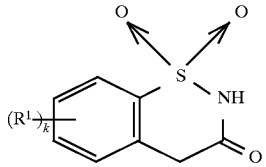

in which $R^1$ and k have the same meanings as defined in the formula (1) can be caused to react with the compound of the formula (7), to give an alkylenediamine derivative having the formula (13):

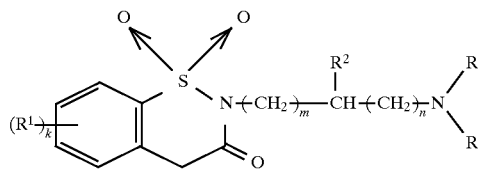

in which $R^1$, $R^2$, $R^3$, $R^4$, k, m, and n have the same meanings as defiend in the formula (1), which belongs to the alkylenediamine derivative of the formula (1).

Furthermore, a compound having the formula (14):

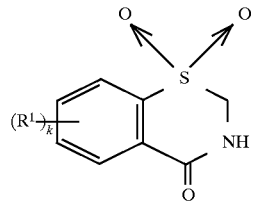

in which $R^1$ and k have the same meanings as defined in the formula (1) can be caused to react with the compound of the formula (7), to give an alkylenediamine derivative having the formula (15):

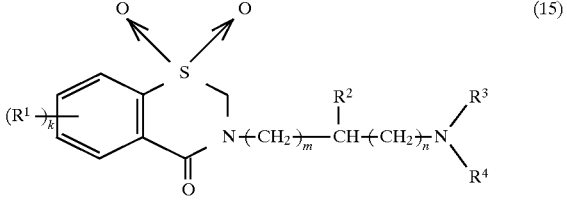

in which $R^1$, $R^2$, $R^3$, $R^4$, k, m, and n have the same meanings as defiend in the formula (1), which belongs to the alkylenediamine derivative of the formula (1).

The reaction conditions for preparing the alkylenediamine derivative of the formula (13) and the alkylenediamine derivative of the formula (15) are almost the same as those adopted for the preparation of the alkylenediamine derivative of the formula (3) starting from the the compound of the formula (10) and the compound of the formula (7).

A compound of the formula (1) in which p is 0 or 1, or q is 0, which is similar to the compound of the formula (13) or the compound of the formula (15) can be synthesized in a manner similar to the above-mentioned process.

The alkylenediamine derivative of the formula (1) can be converted into a pharmacologically acceptable salt. Examples of the pharmacologically acceptable salt of the alkylenediamine derivative of the formula (1) include acid-addition salts such as salts with an inorganic acid (e.g., hydrochloric acid, sulfuric acid, hydrobromic acid, or phosphoric acid), or an organic acid (e.g., fumaric acid, acetic acid, propionic acid, citric acid, tartaric acid, maleic acid, malic acid, oxalic acid, methanesulfonic acid, or p-toluenesulfonic acid).

Examples of the alkylenediamine derivatives represented by the formula (1) are described below:

(1) 2-[3-(4-phenoxypiperidino)propyl]-2H-1,2-benzothiazin-4(3H)-one 1,1-dioxide
(2) 2-[3-(4-benzyloxypiperidino)propyl]-2H-1,2-benzothiazin-4(3H)-one 1,1-dioxide (3) 3-[3-(4-benzylpiperidino)propyl]-1H-2,3-benzothiazin-4(3H)-one 2,2-dioxide
(4) 2-(3-morpholino-1-phenylpropyl)-2H-1,2-benzothiazin-3(4H)-one 1,1-dioxide
(5) 3-(3-morpholino-1-phenylpropyl)-2H-1,3-benzothiazin-4(3H)-one 1,1-dioxide
(6) 3-(2-hydroxy-3-morpholinopropyl)-1H-2,3-benzothiazin-4(3H)-one 2,2-dioxide
(7) 3-(2-ethoxy-3-morpholinopropyl)-1H-2,3-benzothiazin-4(3H)-one 2,2-dioxide
(8) 2-(2-hydroxy-3-morpholinopropyl)-2H-1,2-benzothiazin-4(3H)-one 1,1-dioxide
(9) 3-(3-morpholino-3-phenylpropyl)-1H-2,3-benzothiazin-4(3H)-one 2,2-dioxide
(10) 2-[3-(4-benzylpiperidino)propyl]-2H-1,2-benzothiazin-4(3H)-one 1,1-dioxide
(11) 2-[3-(N-benzyl-N-butylamino)propyl]-2H-1,2-benzothiazin-4(3H)-one 1,1-dioxide
(12) 2-[3-(4-diphenylmethyl-1-piperazinyl)propyl]-2H-1,2-benzothiazin-4(3H)-one 1,1-dioxide
(13) 2-[2-(4-benzylpiperidino)ethyl]-2H-1,2-benzothiazin-4(3H)-one 1,1-dioxide
(14) 2-[3-(4-benzyl-1-piperazinyl)propyl]-2H-1,2-benzothiazin-4(3H)-one 1,1-dioxide
(15) 2-[3-[2-(1,2,3,4-tetrahydroisoquinolyl)]propyl]-2H-1,2-benzothiazin-4(3H)-one 1,1-dioxide
(16) 2-[3-[4-(4-methoxybenzyl)piperidino]propyl]-2H-1,2-benzothiazin-4(3H)-one 1,1-dioxide
(17) 2-(3-morpholinopropyl)-2H-1,2-benzothiazin-4(3H)-one 1,1-dioxide
(18) 2-(3-diethylamino-1-phenylpropyl)-2H-1,2-benzothiazin-4(3H)-one 1,1-dioxide
(19) 2-(1-phenyl-3-piperidinopropyl)-2H-1,2-benzothiazin-4(3H)-one 1,1-dioxide
(20) 2-(3-morpholino-1-phenylpropyl)-2H-1,2-benzothiazin-4(3H)-one 1,1-dioxide
(21) 2-(1-phenyl-3-thiomorpholinopropyl)-2H-1,2-benzothiazin-4(3H)-one 1,1-dioxide
(22) 2-[3-morpholino-1-(4-chlorophenyl)propyl]-2H-1,2-benzothiazin-4(3H)-one 1,1-dioxide
(23) 3-(1-phenyl-3-piperidinopropyl)-1H-2,3-benzothiazin-4(3H)-one 2,2-dioxide
(24) 3-(3-morpholino-1-phenylpropyl)-1H-2,3-benzotiazin-4(3H)-one 2,2-dioxide
(25) 3-(3-diethylamino-1-phenylpropyl)-1H-2,3-benzothiazin-4(3H)-one 2,2-dioxide
(26) 3-(1-phenyl-3-thiomorpholinopropyl)-1H-2,3-benzothiazin-4(3H)-one 2,2-dioxide
(27) 3-[3-morpholino-1-(4-chlorophenyl)propyl]-1H-2,3-benzothiazin-4(3H)-one 2,2-dioxide
(28) 3-(3-morpholino-2-phenylpropyl)-1H-2,3-benzothiazin-4(3H)-one 2,2-dioxide
(29) 2-(3-morpholino-3-phenylpropyl)-2H-1,2-benzothiazin-4(3H)-one 1,1-dioxide
(30) 2-(3-chloropropyl)-2H-1,2-benzothiazin-4(3H)-one 1,1-dioxide
(31) 2-[3-(2,3-dihydro-1H-benz[de]isoquinolin-2-yl)propyl]-2H-1,2-benzothiazin-4(3H)-one 1,1-dioxide hydrochloride
(32) 2-[3-(4-cyano-4-phenylpiperidino)propyl]-2H-1,2-benzothiazin-4(3H)-one 1,1-dioxide fumarate
(33) 2-(3-chloro-1-phenylpropyl)-2H-1,2-benzothiazin-4(3H)-one 1,1-dioxide
(34) 2-[3-(4-cyano-4-phenylpiperidino)-1-phenylpropyl]-2H-1,2-benzothiazin-4(3H)-one 1,1-dioxide fumarate Representative examples of the alkylenediamine derivatives of the invention are set forth in Tables 1 and 2.

In Table 1, the compounds of the formula (2) and the compounds of the formula (3) are given, in which the symbols correspond to those seen in the formulas (2) and (3). In Table 2, the compounds of the formula (13) and the compounds of the formula (15) are given, in which the symbols correspond to those seen in the formulas (13) and (15).

TABLE 1

| $(R^1)_k$ | $R^2$ | $-N<^{R^3}_{R^4}$ | k | m | n |
|---|---|---|---|---|---|
| H | H | morpholino | 1 | 1 | 1 |
| H | H | 4-benzylpiperidino | 1 | 1 | 1 |
| H | H | 4-benzyloxypiperidino | 1 | 1 | 1 |
| H | H | benzylbutylamino | 1 | 1 | 1 |
| H | H | 4-diphenylmethyl-1-piperazinyl | 1 | 1 | 1 |
| H | H | 4-phenoxypiperidino | 1 | 1 | 1 |
| H | H | 4-benzylpiperidino | 1 | 1 | 0 |
| H | H | 4-benzyl-1-piperazinyl | 1 | 1 | 1 |
| H | H | 1,2,3,4-tetrahydroisoquinolin-2-yl | 1 | 1 | 1 |
| H | OH | morpholino | 1 | 1 | 1 |
| H | phenyl | diethylamino | 1 | 0 | 2 |
| H | phenyl | piperidino | 1 | 0 | 2 |
| H | phenyl | morpholino | 1 | 0 | 2 |
| H | phenyl | thiomorpholino | 1 | 0 | 2 |
| H | 4-chlorophenyl | morpholino | 1 | 0 | 2 |
| H | phenyl | morpholino | 1 | 2 | 0 |
| H | H | 4-(4-methoxybenzyl)piperidino | 1 | 1 | 1 |
| H | ethoxy | morpholino | 1 | 1 | 1 |
| H | phenyl | morpholino | 1 | 1 | 1 |
| 5-chloro | H | 4-benzylpiperidino | 1 | 1 | 1 |
| 7-chloro | methyl | 4-benzylpiperidino | 1 | 0 | 2 |
| 5,7-dichloro | H | 4-benzylpiperidino | 2 | 0 | 2 |
| 5-fluoro | H | 4-benzylpiperidino | 1 | 0 | 2 |
| 5-methyl | H | 4-benzylpiperidino | 1 | 0 | 2 |
| 7-fluoro | H | 4-benzylpiperidino | 1 | 0 | 2 |
| 7-methyl | H | 4-benzylpiperidino | 1 | 0 | 2 |
| 5-methoxy | H | 4-benzylpiperidino | 1 | 0 | 2 |

TABLE 1-continued

| (R¹)ₖ | R² | —N(R³)(R⁴) | k | m | n |
|---|---|---|---|---|---|
| 7-methoxy | H | 4-benzylpiperidino | 1 | 0 | 2 |
| 5-chloro | H | 4-benzyl-1-piperazinyl | 1 | 0 | 2 |
| 7-chloro | H | 4-benzyl-1-piperazinyl | 1 | 0 | 2 |
| 5-fluoro | H | 4-benzyl-1-piperazinyl | 1 | 0 | 2 |
| 5-methyl | H | 4-benzyl-1-piperazinyl | 1 | 0 | 2 |
| 5-methoxy | H | 4-benzyl-1-piperazinyl | 1 | 0 | 2 |
| 7-fluoro | H | 4-benzyl-1-piperazinyl | 1 | 0 | 2 |
| 7-methyl | H | 4-benzyl-1-piperazinyl | 1 | 0 | 2 |
| 5-chloro | H | benzylbutylamino | 1 | 0 | 2 |
| 5-fluoro | H | benzylbutylamino | 1 | 0 | 2 |
| 5-methyl | H | benzylbutylamino | 1 | 0 | 2 |
| 5-methoxy | H | benzylbutylamino | 1 | 0 | 2 |
| 5-chloro | H | 1,2,3,4-tetrahydroisoquinolin-2-yl | 1 | 0 | 2 |
| 5-fluoro | H | 1,2,3,4-tetrahydroisoquinolin-2-yl | 1 | 0 | 2 |
| 7-chloro | H | 1,2,3,4-tetrahydroisoquinolin-2-yl | 1 | 0 | 2 |
| 5-methyl | H | 1,2,3,4-tetrahydroisoquinolin-2-yl | 1 | 0 | 2 |
| 5-chloro | H | 4-benzyloxypiperidino | 1 | 0 | 2 |
| 5-fluoro | H | 4-benzyloxypiperidino | 1 | 0 | 2 |
| 7-chloro | H | 4-benzyloxypiperidino | 1 | 0 | 2 |
| 5-methyl | H | 4-benzyloxypiperidino | 1 | 0 | 2 |
| 7-methyl | H | 4-benzyloxypiperidino | 1 | 0 | 2 |
| 5-chloro | H | 4-phenoxypiperidino | 1 | 0 | 2 |
| 5-fluoro | H | 4-phenoxypiperidino | 1 | 0 | 2 |
| 5-methyl | H | 4-phenoxypiperidino | 1 | 0 | 2 |
| 7-chloro | H | 4-phenoxypiperidino | 1 | 0 | 2 |
| 7-methyl | H | 4-phenoxypiperidino | 1 | 0 | 2 |
| 5-chloro | H | 4-diphenylmethyl-1-piperazinyl | 1 | 0 | 2 |
| 5-fluoro | H | 4-diphenylmethyl-1-piperazinyl | 1 | 0 | 2 |
| 5-methyl | H | 4-diphenylmethyl-1-piperazinyl | 1 | 0 | 2 |
| 7-chloro | H | 4-diphenylmethyl-1-piperazinyl | 1 | 0 | 2 |
| 7-methyl | H | 4-diphenylmethyl-1-piperazinyl | 1 | 0 | 2 |
| 5-chloro | H | 4-(4-methoxybenzyl)piperidino | 1 | 0 | 2 |
| 7-methyl | H | 4-(4-methoxybenzyl)piperidino | 1 | 0 | 2 |
| 5-chloro | H | 4-(4-chlorobenzyl)piperidino | 1 | 0 | 2 |
| 7-methyl | H | 4-(4-chlorobenzyl)piperidino | 1 | 0 | 2 |
| 5-chloro | H | 4-(4-acetylbenzyl)piperidino | 1 | 0 | 2 |
| 7-methyl | H | 4-(4-acetylbenzyl)piperidino | 1 | 0 | 2 |
| 5-chloro | H | 4-(4-methylbenzyl)piperidino | 1 | 0 | 2 |
| 7-methyl | H | 4-(4-methylbenzyl)piperidino | 1 | 0 | 2 |
| 5-chloro | H | 4-(3-methoxybenzyl)piperidino | 1 | 0 | 2 |
| 7-methyl | H | 4-(2-chlorobenzyl)piperidino | 1 | 0 | 2 |
| 5-chloro | H | 3-benzylpiperidino | 1 | 0 | 2 |
| 7-methyl | H | 3-benzylpiperidino | 1 | 0 | 2 |
| 5-chloro | H | 4-(4-methoxybenzyl)-1-piperazinyl | 1 | 0 | 2 |
| 5-methyl | H | 4-(4-methoxybenzyl)-1-piperazinyl | 1 | 0 | 2 |
| 7-methyl | H | 4-(4-chlorobenzyl)-1-piperazinyl | 1 | 0 | 2 |
| 5-chloro | H | 6-methoxy-1,2,3,4-tetrahydroisoquinolin-2-yl | 1 | 0 | 2 |
| 7-methyl | H | 6-methoxy-1,2,3,4-tetrahydroisoquinolin-2-yl | 1 | 0 | 2 |
| 5-chloro | H | 6-chloro-1,2,3,4-tetrahydroisoquinolin-2-yl | 1 | 0 | 2 |
| 7-methyl | H | 6-chloro-1,2,3,4-tetrahydroisoquinolin-2-yl | 1 | 0 | 2 |
| 5-chloro | H | 4-(4-methoxybenzyl)oxypiperidino | 1 | 0 | 2 |
| 5-chloro | H | 4-(4-chlorobenzyl)oxypiperidino | 1 | 0 | 2 |
| 5-chloro | H | 4-(4-methoxybenzyl)phenoxypiperidino | 1 | 0 | 2 |
| 5-chloro | H | 4-(4-chlorobenzyl)phenoxypiperidino | 1 | 0 | 2 |
| H | H | 4-(4-methoxybenzyl)piperidino | 1 | 0 | 2 |
| H | H | 4-(4-chlorobenzyl)piperidino | 1 | 0 | 2 |
| H | H | 4-(4-acetylbenzyl)piperidino | 1 | 0 | 2 |
| H | H | 4-(4-methylbenzyl)piperidino | 1 | 0 | 2 |
| H | H | 4-(3-methoxybenzyl)piperidino | 1 | 0 | 2 |
| H | H | 4-(2-chlorobenzyl)piperidino | 1 | 0 | 2 |
| H | H | 3-benzylpiperidino | 1 | 0 | 2 |
| H | H | 4-(4-methoxybenzyl)-1-piperazinyl | 1 | 0 | 2 |
| H | H | 4-(4-chlorobenzyl)-1-piperazinyl | 1 | 0 | 2 |
| H | H | 6-methoxy-1,2,3,4-tetrahydroisoquinolin-2-yl | 1 | 0 | 2 |
| H | H | 6-chloro-1,2,3,4-tetrahydroisoquinolin-2-yl | 1 | 0 | 2 |
| H | H | 4-diphenylmethyloxypiperidino | 1 | 0 | 2 |
| 5-chloro | H | 4-diphenylmethyloxypiperidino | 1 | 0 | 2 |
| 7-methyl | H | 4-diphenylmethyloxypiperidino | 1 | 0 | 2 |
| H | H | 3-benzylthiopiperidino | 1 | 0 | 2 |
| H | H | 3-phenylthiopiperidino | 1 | 0 | 2 |
| H | phenyl | morpholino | 1 | 0 | 1 |
| H | phenyl | morpholino | 1 | 0 | 3 |
| H | phenyl | 4-acetyl-1-piperazinyl | 1 | 0 | 2 |
| H | 4-chlorophenyl | morpholino | 1 | 0 | 2 |
| H | 4-methylphenyl | morpholino | 1 | 0 | 2 |

TABLE 1-continued

| $(R^1)_k$ | $R^2$ | $-\overset{R^3}{\underset{|}{N}}-R^4$ | k | m | n |
|---|---|---|---|---|---|
| H | 3-chlorophenyl | morpholino | 1 | 0 | 2 |
| H | 2-chlorophenyl | morpholino | 1 | 0 | 2 |
| H | 2,4-dichlorophenyl | thiomorpholino | 1 | 0 | 2 |
| H | 4-chlorophenyl | thiomorpholino | 1 | 0 | 2 |
| H | 4-methylphenyl | thiomorpholino | 1 | 0 | 2 |
| H | 3-chlorophenyl | thiomorpholino | 1 | 0 | 2 |
| H | 2-chlorophenyl | thiomorpholino | 1 | 0 | 2 |
| H | 2,4-dichlorophenyl | thiomorpholino | 1 | 0 | 2 |
| H | 4-fluorophenyl | thiomorpholino | 1 | 0 | 2 |
| H | 4-fluorophenyl | morpholino | 1 | 0 | 2 |
| 5-chloro | phenyl | morpholino | 1 | 0 | 2 |
| 5-chloro | phenyl | thiomorpholino | 1 | 0 | 2 |
| 5-fluoro | phenyl | morpholino | 1 | 0 | 2 |
| 7-chloro | phenyl | morpholino | 1 | 0 | 2 |
| 5-methyl | phenyl | morpholino | 1 | 0 | 2 |
| 7-methyl | phenyl | morpholino | 1 | 0 | 2 |
| 7-fluoro | phenyl | morpholino | 1 | 0 | 2 |
| 5,7-dichloro | phenyl | morpholino | 2 | 0 | 2 |
| 5-chloro | 4-chlorophenyl | morpholino | 1 | 0 | 2 |
| 5-chloro | 3-chlorophenyl | morpholino | 1 | 0 | 2 |
| 5-chloro | 2-chlorophenyl | morpholino | 1 | 0 | 2 |
| 5-chloro | phenyl | 4-acetyl-1-piperazinyl | 1 | 0 | 2 |
| H | phenyl | 4-benzyl-1-piperazinyl | 1 | 0 | 2 |
| H | OH | morpholino | 1 | 0 | 2 |
| H | ethoxy | morpholino | 1 | 0 | 2 |
| H | methyl | 4-benzylpiperidino | 1 | 0 | 2 |
| H | phenyl | 4-benzylpiperidino | 1 | 0 | 2 |
| H | 2-thienyl | morpholino | 1 | 0 | 2 |
| H | 2-furyl | morpholino | 1 | 0 | 2 |
| H | 2-furyl | 4-benzylpiperidino | 1 | 0 | 2 |
| H | H | 4-(2-thienylmethyl)piperidino | 1 | 0 | 2 |
| H | H | 4-(2-thienylmethyl)piperidino | 1 | 0 | 3 |
| H | allyl | morpholino | 1 | 0 | 2 |
| H | phenyl | benzylbutylamino | 1 | 0 | 2 |
| 5-chloro | H | 4-(2-thienylmethyl)piperidino | 1 | 0 | 2 |
| 5-chloro | 4-chlorophenyl | 4-diphenylmethyl-1-piperazinyl | 1 | 0 | 2 |
| 5-chloro | 4-chlorophenyl | diethylamino | 1 | 0 | 2 |
| 5-chloro | 4-chlorophenyl | diethylamino | 1 | 0 | 3 |
| H | 2-pyridyl | thiomorpholino | 1 | 0 | 2 |
| 7-chloro | 2-pyridyl | 2-benzylpiperidino | 1 | 0 | 2 |
| H | H | 2,3-dihydro-1H-benz[de]-isoquinolin-2-yl | 1 | 1 | 1 |
| H | H | 4-phenylpiperidino | 1 | 1 | 1 |
| H | H | 4-phenyl-1-piperazinyl | 1 | 1 | 1 |
| H | H | 4-(2-thienylmethoxy)piperidino | 1 | 1 | 1 |
| H | H | 4-(2-thienylmethyl)piperidino | 1 | 1 | 1 |
| H | H | 4-(2-thienyl)-1-piperazinyl | 1 | 1 | 1 |

TABLE 2

| $(R^1)_k$ | $R^2$ | $-\overset{R^3}{\underset{|}{N}}-R^4$ | k | m | n |
|---|---|---|---|---|---|
| H | phenyl | morpholino | 1 | 0 | 2 |
| H | H | 4-benzylpiperidino | 1 | 0 | 2 |
| H | H | 4-diphenyl-1-piperazinyl | 1 | 0 | 2 |
| H | H | 4-benzylpiperidino | 1 | 0 | 1 |
| H | H | 4-benzylpiperidino | 1 | 0 | 3 |
| 5-chloro | H | 4-benzylpiperidino | 1 | 0 | 2 |
| H | phenyl | thiomorpholino | 1 | 0 | 2 |
| H | 2-thienyl | morpholino | 1 | 0 | 2 |
| H | H | 6-chloro-1,2,3,4-tetrahydro-isoquinolin-2-yl | 1 | 0 | 2 |
| 7-chloro | H | 6-chloro-1,2,3,4-tetrahydro-isoquinolin-2-yl | 1 | 0 | 2 |
| 5,7-dichloro | phenyl | diethylamino | 2 | 0 | 2 |
| H | 4-chlorophenyl | morpholino | 1 | 0 | 2 |
| 5-chloro | ethoxy | 4-benzylpiperidino | 1 | 1 | 1 |

Next, in the formula (I), the halogen represented by $R^1$ preferably is fluorine, chlorine or bromine, and chlorine is most preferred. The alkyl having 1–8 carbon atoms which is represented by $R^1$ preferably is methyl, ethyl, propyl, isopropyl, butyl, isobutyl, pentyl, hexyl, heptyl, or octyl. The haloalkyl having 1–4 carbon atoms preferably is trifluoromethyl, chloromethyl, or fluoromethyl. The alkoxy having 1–8 carbon atoms preferably is methoxy, ethoxy, or propoxy. The aryloxy having 4–10 carbon atoms (which may have nucleus substituents such as halogen, cyano, alkyl, alkoxy, amino, or alkoxycarbonyl) preferably is phenoxy or p-chlorophenoxy. The aralkyloxy having 5–14 carbon atoms (its alkyl portion has 1–4 carbon atoms) preferably is benzyloxy, pyridylmethyloxy, naphthylmethyloxy, or thenyloxy. The alkylamino having 1–8 carbon atoms preferably is methylamino, dimethylamino, ethylamino, propylamino, or isobutylamino. The aralkylamino having 5–14 carbon atoms (its alkyl portion has 1–4 carbon atoms, and which may have nucleus substituents such as halogen, cyano, alkyl, alkoxy, amino, or alkoxycarbonyl) preferably is benzylamino or (4-chlorophenyl)methylamino. The arylamino having 4–10 carbon atoms (which may have nucleus substituents such as halogen, cyano, alkyl, alkoxy, amino, or alkoxycarbonyl) preferably is phenylamino or p-chlorophenylamino. The aliphatic acylamino having 1–8 carbon atom preferably is acetylamino or propionylamino. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, naphthyloxycarbonyl, or thienyloxycarbonyl. The alkoxysulfonyl having 1–8 carbon atoms preferably is methoxysulfonyl or ethoxysulfonyl. The aralkyloxysulfonyl having 5–14 carbon atoms (its alkyl portion has 1–4 carbon atoms) preferably is benzyloxysulfonyl, naphthylmethyloxysulfonyl, or thenyloxysulfonyl. The aryloxysulfonyl having 4–10 carbon atoms preferably is phenoxysulfonyl, naphthyloxysulfonyl, or thienyloxysulfonyl.

In the formula (I), particularly preferred for $R^1$ is hydrogen, halogen, or alkoxy having 1–8 carbon atoms.

In the formula (I), $R^2$ represents a phenyl, naphthyl, or aromatic heterocyclic group which may have one to five same or different substituents. Preferred groups are phenyl, naphthyl, furan, thiophene, pyridine, quinoline, or indole, which may have one to five same or different substituents.

Among the above-mentioned substituents, the halogen preferably is fluorine, chlorine, or bromine. The alkyl having 1–8 carbon atoms preferably is methyl, ethyl, propyl, isopropyl, butyl, isobutyl, pentyl, hexyl, heptyl, or octyl. The haloalkyl having 1–4 carbon atoms preferably is trifluoromethyl, chloromethyl, or fluoromethyl. The alkoxy having 1–8 carbon atoms preferably is methoxy, ethoxy, or propoxy. The aryloxy having 4–10 carbon atoms (which may have nucleus substituents such as halogen, cyano, alkyl, alkoxy, amino, or alkoxycarbonyl) preferably is phenoxy or p-chlorophenoxy. The aralkyloxy having 5–14 carbon atoms (its alkyl portion has 1–4 carbon atoms) preferably is benzyloxy, pyridylmethyloxy, naphthylmethyloxy, or thenyloxy. The alkylamino having 1–8 carbon atoms preferably is methylamino, dimethylamino, ethylamino, propylamino, or isobutylamino. The aralkylamino having 5–14 carbon atoms (its alkyl portion has 1–4 carbon atoms, and which may have nucleus substituents such as halogen, cyano, alkyl, alkoxy, amino, or alkoxycarbonyl) preferably is benzylamino or (4-chlorophenyl)methylamimo. The arylamino having 4–10 carbon atoms (which may have nucleus substituents such as halogen, cyano, alkyl, alkoxy, amino, or alkoxycarbonyl) preferably is phenylamino or p-chlorophenylamino. The aliphatic acylamino having 1–8 carbon atom preferably is acetylamino or propionylamino. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, pyridyloxycarbonyl, naphthyloxycarbonyl, or thienyloxycarbonyl. The alkoxysulfonyl having 1–8 carbon atoms preferably is methoxysulfonyl or ethoxysulfonyl. The aralkyloxysulfonyl having 5–14 carbon atoms (its alkyl portion has 1–4 carbon atoms) preferably is benzyloxysulfonyl, naphthylmethyloxysulfonyl, or thenyloxysulfonyl. The aryloxysulfonyl having 4–10 carbon atoms preferably is phenoxysulfonyl, naphthyloxysulfonyl, or thienyloxysulfonyl.

Preferred for $R^2$ is phenyl or thienyl which may have one to five same or different substituents. More preferred is phenyl having no substituents, or phenyl having, as substituent, one to five of alkyl having 1–8 carbon atoms, alkoxy having 1–8 carbon atoms, halogen, or haloalkyl having 1–8 carbon atoms. Particularly preferred is phenyl having no substituents or phenyl having one substituent such as halogen or alkoxy having 1–8 carbon atoms.

In the formula (I), the alkyl having 1–8 carbon atoms which is represented by $R^3$ or $R^4$ preferably is methyl, ethyl, propyl, isopropyl, butyl, or isobutyl. The aralkyl having 5–14 carbon atoms (its alkyl portion has 1–4 carbon atoms) preferably is benzyl, phenylethyl, or phenylpropyl. The aryl having 4–10 carbon atoms preferably is phenyl, pyridyl, or naphthyl.

The five to seven membered heterocyclic group represented by the formula (II) formed by the combination of $R^3$, $R^4$ and the nitrogen atom to which $R^3$ and $R^4$ are attached preferably is morpholino, piperidino, homomorpholino, 1-pyrrolidinyl, thiomorpholino, 1-piperazinyl, 1-perhydroazepinyl, S-oxythiomorpholino, or S,S-dioxythiomorpholino.

The alkyl having 1–8 carbon atoms which is represented by $R^5$ of the formula (III) for Z of the formula (II) preferably is methyl, ethyl, propyl, isopropyl, butyl, or isobutyl. The aralkyl having 5–14 carbon atoms (its alkyl has 1–4 carbon atoms) preferably is benzyl, phenylethyl, or phenylpropyl. The alkoxycarbonyl having 2–9 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, naphthyloxycarbonyl, or thienyloxycarbonyl.

Among the substituents which may be attached to the five to seven membered heterocyclic group of the formula (II), the alkyl having 1–5 carbon atoms preferably is methyl, ethyl, propyl, isopropyl, butyl, or isobutyl. The aralkyl having 5–14 (its alkyl portion has 1–4 carbon atom) preferably is benzyl, phenylethyl, or phenylpropyl. The alkoxy having 1–5 carbon atoms preferably is methoxy, ethoxy, or propoxy. The alkoxycarbonyl having 2–6 carbon atoms preferably is methoxycarbonyl, ethoxycarbonyl, or propoxycarbonyl. The aralkyloxycarbonyl having 6–15 carbon atoms (its alkyl portion has 1–4 carbon atoms) preferably is benzyloxycarbonyl, pyridylmethyloxycarbonyl, naphthylmethyloxycarbonyl, or thenyloxycarbonyl. The aryloxycarbonyl having 5–11 carbon atoms preferably is phenoxycarbonyl, naphthyloxycarbonyl, or thienyloxycarbonyl. The aliphatic acyl having 1–8 carbon atoms preferably is formyl, acetyl, or propionyl. The aromatic acyl having 5–11 carbon atoms preferably is benzoyl or phthaloyl. If the two or more substituents are attached, these substituents may be the same or different.

The five to seven membered heterocyclic group represented by the formula (II) preferably is morpholino, piperidino, homomorpholino, 1-pyrrolidinyl, thiomorpholino, 1-piperazinyl, 1-perhydroazepinyl, S-oxythiomorpholino, or S,S-dioxythiomorpholino which may not have substituents or may have substituents such as alkyl having 1–8 carbon atoms, phenyl, acyl having 1–8 carbon atoms, carbamoyl, or 2-pyrimidinyl on its carbon and/or nitrogen atom.

In the formula (I), m preferably is 1 or 2, and 1 is most preferred. n preferably is 0, 1, or 2, and 0 is most preferred. p preferably is 0, and q preferably is 1, 2 or 3. The alkylenediamine derivative of the formula (I) in which x is 2 and y is 1 corresponds to the alkylenediamine derivative of the formula (IV). The alkylenediamine derivative of the formula (I) in which x is 1 and y is 1 corresponds to the alkylenediamine derivative of the formula (V). The alkylenediamine derivative of the formula (I) in which x is 2 and y is 0 corresponds to the alkylenediamine derivative of the formula (VI).

The alkylenediamine derivative of the formula (I) can be prepared by reacting a compound having the formula (VII):

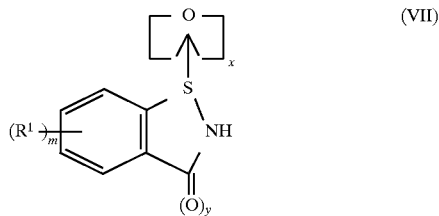

in which $R^1$, m, x and y have the same meanings as defined in the formula (I)

with a compound having the formula (VIII):

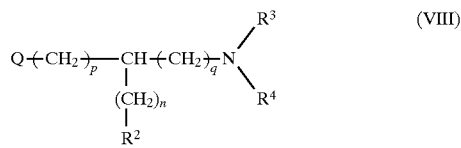

in which $R^2$, $R^3$, $R^4$, n, p and q have the same meanings as defined in the formula (I), and Q is a releasable group such as halogen, tosyloxy, or mesyloxy.

In the above-mentioned preparation process, the compound of the formula (VII) and the compound of the formula (VIII) are caused to react at a temperature from room temperature to the reflux temperature for 1 to 50 hours, in an organic solvent such as acetone, dimethylformamide, methyl ethyl ketone, or isobutyl methyl ketone, in the presence of a carbonate such as potassium carbonate, sodium carbonate, or cesium carbonate, to prepare the compound of the formula (I). In the reaction, 1 to 2 moles of the compound of the formula (VIII) and the 2 to 8 moles of the carbonate are preferably employed per one mole of the compound of the formula (VII). The compound of the formula (VIII) is preferably employed in its stable hydrochloride form.

Alternatively, the alkylenediamine derivative of the formula (I) can be prepared by reacting a compound of the formula (IX):

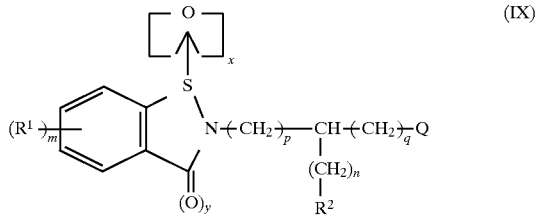

in which $R^1$, $R^2$, m, n, p, q, x and y have the same meanings as defined in the formula (I), and Q is a releasable group such as halogen, tosyloxy, or mesyloxy, with a compound having the formula (X):

in which $R^3$ and $R^4$ have the same meanings as defined in the formula (I).

In the above-mentioned preparation process, the compound of the formula (IX) and the compound of the formula (X) are caused to react at 50° to 150° C. for 1 to 20 hours, generally, in the absence of a solvent. If necessary, a solvent which does not participate in the reaction can be employed.

The alkylenediamine derivative of the formula (I) can be converted into a pharmacologically acceptable salt. Examples of the pharmacologically acceptable salt of the alkylenediamine derivative of the formula (I) include acid-addition salts such as salts with an inorganic acid (e.g., hydrochloric acid, sulfuric acid, hydrobromic acid, or phosphoric acid), or an organic acid (e.g., fumaric acid, acetic acid, propionic acid, citric acid, tartaric acid, maleic acid, malic acid, oxalic acid, methanesulfonic acid, or p-toluenesulfonic acid).

Examples of the alkylenediamine derivatives represented by the formula (I) are described below:

(1) 2-[1-phenyl-3-(1-pyrrolidinyl)]propyl-1,2-benzisothiazol-3(2H)-one 1,1-dioxide
(2) 2-(1-phenyl-3-thiomorpholino)propyl-1,2-benzisothiazol-3(2H)-one 1,1-dioxide
(3) 2-(2-morpholino-1-phenyl)ethyl-1,2-benzisothiazol-3(2H)-one 1,1-dioxide
(4) 2-(4-morpholino-1-phenyl)butyl-1,2-benzisothiazol-3(2H)-one 1,1-dioxide
(5) 2-(1-phenyl-3-piperidino)propyl-1,2-benzisothiazol-3(2H)-one 1,1-dioxide
(6) 2-[3-(perhydroazepin-1-yl)-1-phenyl]propyl-1,2-benzisothiazol-3(2H)-one 1,1-dioxide
(7) 2-[3-(4-methylpiperidino)-1-phenyl]propyl-1,2-benzisothiazol-3(2H)-one 1,1-dioxide
(8) 2-[3-(4-carbamoylpiperidino)-1-phenyl]propyl-1,2-benzisothiazol-3(2H)-one 1,1-dioxide
(9) 2-(3-morpholino-1-phenyl)propyl-1,2-benzisothiazol-3(2H)-one 1,1-dioxide
(10) 2-[3-(4-ethyl-1-piperazinyl)-1-phenyl]propyl-1,2-benzisothiazol-3(2H)-one 1,1-dioxide
(11) 2-[3-(4-acetyl-1-piperazinyl)-1-phenyl]propyl-1,2-benzisothiazol-3(2H)-one 1,1-dioxide
(12) 2-[1-phenyl-3-(4-(2-pyrimidinyl)-1-piperazinyl]propyl-1,2-benzisothiazol-3(2H)-one 1,1-dioxide
(13) 2-[1-(4-chlorophenyl)-3-piperidino]propyl-1,2-benzisothiazol-3(2H)-one 1,1-dioxide
(14) 2-[1-(4-chlorophenyl)-3-morpholino]propyl-1,2-benzisothiazol-3(2H)-one 1,1-dioxide
(15) 2-[1-(4-methoxyphenyl)-3-piperidino]propyl-1,2-benzisothiazol-3(2H)-one 1,1-dioxide
(16) 6-chloro-2-(1-phenyl-3-piperidino)propyl-1,2-benzisothiazol-3(2H)-one 1,1-dioxide
(17) 6-chloro-2-(3-morpholino-1-phenyl)propyl-1,2-benzisothiazol-3(2H)-one 1,1-dioxide
(18) 6-methoxy-2-(1-phenyl-3-piperidino)propyl-1,2-benzisothiazol-3(2H)-one 1,1-dioxide
(19) 6-methoxy-2-(3-morpholino-1-phenyl)propyl-1,2-benzisothiazol-3(2H)-one 1,1-dioxide
(20) 4-chloro-2-(3-piperidino-1-phenyl)propyl-1,2-benzisothiazol-3(2H)-one 1,1-dioxide
(21) 2-(1-phenyl-3-thiomorpholino)propyl-1,2-benzisothiazol-3(2H)-one 1,1,S-trioxide
(22) 2-(1-phenyl-3-thiomorpholino)propyl-1,2-benzisothiazol-3(2H)-one 1,1,S,S-tetraoxide

(23) 2-[3-(2-nethylthiomorpholino)-1-phenyl]propyl-1,2-benzisothiazol-3(2H)-one 1,1-dixoide
(24) 2-[3-(3-methylthiomorpholino)-1-phenyl]propyl-1,2-benzisothiazol-3(2H)-one 1,1-dixoide
(25) 2-[3-(2,2-dimethylthiomorpholino)-1-phenyl]propyl-1,2-benzisothiazol-3(2H)-one 1,1-dioxide
(26) 2-[3-(2,6-dimethylthiomorpholino)-1-phenyl]propyl-1,2-benzisothiazol-3(2H)-one 1,1-dioxide
(27) 2-[1-phenyl-3-(2-phenylthiomorpholino)]propyl-1,2-benzisothiazol-3(2H)-one 1,1-dioxide
(28) 2-[1-(4-fluorophenyl)-3-thiomorpholino]propyl-1,2-benzisothiazol-3(2H)-one 1,1-dioxide
(29) 2-(3-dimethylamino-1-phenyl)propyl-1,2-benzisothiazol-3(2H)-one 1,1-dioxide
(30) 2-(3-diethylamino-1-phenyl)propyl-1,2-benzisothiazol-3(2H)-one 1,1-dioxide
(31) 2-(3-benzylethylamino-1-phenyl)propyl-1,2-benzisothiazol- 3(2H)-one 1,1-dioxide
(32) 2-(3-morpholino-1-phenyl)propyl-1,2-benzisothiazol-3(2H)-one 1-oxide
(33) 2-(3-piperidino-1-phenyl)propyl-1,2-benzisothiazoline 1,1-dioxide
(34) 2-(3-morpholino-1-phenyl)propyl-1,2-benzisothiazoline 1,1-dioxide Representative examples of the alkylenediamine derivatives of the formula (I) according to the invention are set forth in Tables 3, in which the symbols correspond to those seen in the formula (I).

TABLE 3

| No. | $(R^1)_m$ | $R^2$ | $-NR^3R^4$ | m | n | p | q | x | y |
|---|---|---|---|---|---|---|---|---|---|
| 1 | H | phenyl | 1-pyrrolidinyl | 1 | 0 | 0 | 2 | 2 | 1 |
| 2 | H | phenyl | thiomorpholino | 1 | 0 | 0 | 2 | 2 | 1 |
| 3 | H | phenyl | morpholino | 1 | 0 | 0 | 1 | 2 | 1 |
| 4 | H | phenyl | morpholino | 1 | 0 | 0 | 3 | 2 | 1 |
| 5 | H | phenyl | piperidino | 1 | 0 | 0 | 2 | 2 | 1 |
| 6 | H | phenyl | 1-perhydroazepinyl | 1 | 0 | 0 | 2 | 2 | 1 |
| 7 | H | phenyl | 4-methylpiperidino | 1 | 0 | 0 | 2 | 2 | 1 |
| 8 | H | phenyl | 4-carbamoyl-piperidino | 1 | 0 | 0 | 2 | 2 | 1 |
| 9 | H | phenyl | morpholino | 1 | 0 | 0 | 2 | 2 | 1 |
| 10 | H | phenyl | 4-ethyl-1-piperazinyl | 1 | 0 | 0 | 2 | 2 | 1 |
| 11 | H | phenyl | 4-acetyl-1-piperazinyl | 1 | 0 | 0 | 2 | 2 | 1 |
| 12 | H | phenyl | 4-(2-pyrimidinyl)-1-piperazinyl | 1 | 0 | 0 | 2 | 2 | 1 |
| 13 | H | 4-chloro-phenyl | piperidino | 1 | 0 | 0 | 2 | 2 | 1 |
| 14 | H | 4-chloro-phenyl | morpholino | 1 | 0 | 0 | 2 | 2 | 1 |
| 15 | H | 4-methoxy-phenyl | piperidino | 1 | 0 | 0 | 2 | 2 | 1 |
| 16 | 6-chloro | phenyl | piperidino | 1 | 0 | 0 | 2 | 2 | 1 |
| 17 | 6-chloro | phenyl | morpholino | 1 | 0 | 0 | 2 | 2 | 1 |
| 18 | 6-methoxy | phenyl | piperidino | 1 | 0 | 0 | 2 | 2 | 1 |
| 19 | 6-methoxy | phenyl | morpholino | 1 | 0 | 0 | 2 | 2 | 1 |
| 20 | 4-chloro | phenyl | piperidino | 1 | 0 | 0 | 2 | 2 | 1 |
| 21 | H | phenyl | thiomorpholino-oxide | 1 | 0 | 0 | 2 | 2 | 1 |
| 22 | H | phenyl | thiomorpholino-dioxide | 1 | 0 | 0 | 2 | 2 | 1 |
| 23 | H | phenyl | 2-methylthio-morpholino | 1 | 0 | 0 | 2 | 2 | 1 |
| 24 | H | phenyl | 3-methylthio-morpholino | 1 | 0 | 0 | 2 | 2 | 1 |
| 25 | H | phenyl | 2,2-dimethyl-thiomorpholino | 1 | 0 | 0 | 2 | 2 | 1 |
| 26 | H | phenyl | 2,6-dimethyl-thiomorpholino | 1 | 0 | 0 | 2 | 2 | 1 |
| 27 | H | phenyl | 2-phenylthio-morpholino | 1 | 0 | 0 | 2 | 2 | 1 |
| 28 | H | 4-fluoro-phenyl | thiomorpholino | 1 | 0 | 0 | 2 | 2 | 1 |
| 29 | H | phenyl | dimethylamino | 1 | 0 | 0 | 2 | 2 | 1 |
| 30 | H | phenyl | diethylamino | 1 | 0 | 0 | 2 | 2 | 1 |
| 31 | H | phenyl | benzylethylamino | 1 | 0 | 0 | 2 | 2 | 1 |
| 32 | H | phenyl | morpholino | 1 | 0 | 0 | 2 | 1 | 1 |
| 33 | H | phenyl | piperidino | 1 | 0 | 0 | 2 | 2 | 0 |
| 34 | H | phenyl | morpholino | 1 | 0 | 0 | 2 | 2 | 0 |
| 35 | 4-bromo | phenyl | morpholino | 1 | 0 | 0 | 2 | 2 | 1 |
| 36 | 6-bromo | phenyl | morpholino | 1 | 0 | 0 | 2 | 2 | 1 |
| 37 | 4-fluoro | phenyl | morpholino | 1 | 0 | 0 | 2 | 2 | 1 |
| 38 | 6-fluoro | phenyl | morpholino | 1 | 0 | 0 | 2 | 2 | 1 |
| 39 | 4-methoxy | phenyl | morpholino | 1 | 0 | 0 | 2 | 2 | 1 |
| 40 | 4-cyano | phenyl | morpholino | 1 | 0 | 0 | 2 | 2 | 1 |
| 41 | 4-methyl | phenyl | morpholino | 1 | 0 | 0 | 2 | 2 | 1 |
| 42 | 6-cyano | phenyl | morpholino | 1 | 0 | 0 | 2 | 2 | 1 |
| 43 | 6-methyl | phenyl | morpholino | 1 | 0 | 0 | 2 | 2 | 1 |

TABLE 3-continued

| No. | (R¹)ₘ | R² | —NR³R⁴ | m | n | p | q | x | y |
|---|---|---|---|---|---|---|---|---|---|
| 44 | 4-hydroxy | phenyl | morpholino | 1 | 0 | 0 | 2 | 2 | 1 |
| 45 | 6-phenoxy | phenyl | morpholino | 1 | 0 | 0 | 2 | 2 | 1 |
| 46 | 4-acetyl-amino | phenyl | morpholino | 1 | 0 | 0 | 2 | 2 | 1 |
| 47 | H | 2-thienyl | morpholino | 1 | 0 | 0 | 2 | 2 | 1 |
| 48 | 4-chloro | 2-thienyl | morpholino | 1 | 0 | 0 | 2 | 2 | 1 |
| 49 | 4-bromo | 2-thienyl | morpholino | 1 | 0 | 0 | 2 | 2 | 1 |
| 50 | 4-fluoro | 2-thienyl | morpholino | 1 | 0 | 0 | 2 | 2 | 1 |
| 51 | 4-methoxy | 2-thienyl | morpholino | 1 | 0 | 0 | 2 | 2 | 1 |
| 52 | H | 2-furyl | morpholino | 1 | 0 | 0 | 2 | 2 | 1 |
| 53 | 4-chloro | 2-furyl | morpholino | 1 | 0 | 0 | 2 | 2 | 1 |
| 54 | 4-bromo | 2-furyl | morpholino | 1 | 0 | 0 | 2 | 2 | 1 |
| 55 | 4-fluoro | 2-furyl | morpholino | 1 | 0 | 0 | 2 | 2 | 1 |
| 56 | 4-methoxy | 2-furyl | morpholino | 1 | 0 | 0 | 2 | 2 | 1 |
| 57 | 4-chloro | phenyl | thiomorpholino | 1 | 0 | 0 | 2 | 2 | 1 |
| 58 | 4-bromo | phenyl | thiomorpholino | 1 | 0 | 0 | 2 | 2 | 1 |
| 59 | 4-fluoro | phenyl | thiomorpholino | 1 | 0 | 0 | 2 | 2 | 1 |
| 60 | 4-methoxy | phenyl | thiomorpholino | 1 | 0 | 0 | 2 | 2 | 1 |
| 61 | H | 2-thienyl | thiomorpholino | 1 | 0 | 0 | 2 | 2 | 1 |
| 62 | H | 2-furyl | thiomorpholino | 1 | 0 | 0 | 2 | 2 | 1 |
| 63 | H | phenyl | morpholino | 1 | 0 | 1 | 1 | 2 | 1 |
| 64 | H | phenyl | morpholino | 1 | 0 | 2 | 0 | 2 | 1 |
| 65 | H | phenyl | thiomorpholino | 1 | 0 | 1 | 1 | 2 | 1 |
| 66 | H | phenyl | thiomorpholino | 1 | 0 | 2 | 0 | 2 | 1 |
| 67 | H | phenyl | homomorpholino | 1 | 0 | 0 | 2 | 2 | 1 |
| 68 | 4-chloro | phenyl | homomorpholino | 1 | 0 | 0 | 2 | 2 | 1 |
| 69 | 4-bromo | phenyl | homomorpholino | 1 | 0 | 0 | 2 | 2 | 1 |
| 70 | 4-fluoro | phenyl | homomorpholino | 1 | 0 | 0 | 2 | 2 | 1 |
| 71 | 4-methoxy | phenyl | homomorpholino | 1 | 0 | 0 | 2 | 2 | 1 |
| 72 | 5,6-dichloro | phenyl | morpholino | 2 | 0 | 0 | 2 | 2 | 1 |
| 73 | 5,6-dichloro | phenyl | thiomorpholino | 2 | 0 | 0 | 2 | 2 | 1 |
| 74 | 5,6-dichloro | phenyl | piperidino | 2 | 0 | 0 | 2 | 2 | 1 |
| 75 | 5,6-dichloro | phenyl | homomorpholino | 2 | 0 | 0 | 2 | 2 | 1 |
| 76 | 5,6-dimethoxy | phenyl | morpholino | 2 | 0 | 0 | 2 | 2 | 1 |
| 77 | 5,6-dimethoxy | phenyl | thiomorpholino | 2 | 0 | 0 | 2 | 2 | 1 |
| 78 | 5,6-dimethoxy | phenyl | piperidino | 2 | 0 | 0 | 2 | 2 | 1 |
| 79 | 5,6-dimethoxy | phenyl | homomorpholino | 2 | 0 | 0 | 2 | 2 | 1 |
| 80 | 4-chloro | 4-chloro-phenyl | morpholino | 1 | 0 | 0 | 2 | 2 | 1 |
| 81 | 4-chloro | 4-chloro-phenyl | thiomorpholino | 1 | 0 | 0 | 2 | 2 | 1 |
| 82 | 4-chloro | 4-chloro-phenyl | piperidino | 1 | 0 | 0 | 2 | 2 | 1 |
| 83 | 4-bromo | 4-chloro-phenyl | morpholino | 1 | 0 | 0 | 2 | 2 | 1 |
| 84 | 4-bromo | 4-chloro-phenyl | thiomorpholino | 1 | 0 | 0 | 2 | 2 | 1 |
| 85 | 4-bromo | 4-fluoro-phenyl | morpholino | 1 | 0 | 0 | 2 | 2 | 1 |
| 86 | 4-fluoro | 4-chloro-phenyl | morpholino | 1 | 0 | 0 | 2 | 2 | 1 |
| 87 | 4-fluoro | 4-chloro-phenyl | thiomorpholino | 1 | 0 | 0 | 2 | 2 | 1 |
| 88 | H | 2,6-dichloro-phenyl | morpholino | 1 | 0 | 0 | 2 | 2 | 1 |
| 89 | H | 3,5-dichloro-phenyl | morpholino | 1 | 0 | 0 | 2 | 2 | 1 |
| 90 | H | 2,6-dichloro-phenyl | thiomorpholino | 1 | 0 | 0 | 2 | 2 | 1 |
| 91 | H | 3,5-dichloro-phenyl | thiomorpholino | 1 | 0 | 0 | 2 | 2 | 1 |
| 92 | 4-methyl | 4-chloro | morpholino | 1 | 0 | 0 | 2 | 2 | 1 |
| 93 | 4-chloro | 4-methyl | morpholino | 1 | 0 | 0 | 2 | 2 | 1 |
| 94 | 5,6-dichloro | 2,6-dichloro-phenyl | morpholino | 2 | 0 | 0 | 2 | 2 | 1 |
| 95 | 4-chloro | 4-chlorophenyl | morpholino | 1 | 0 | 1 | 1 | 2 | 1 |
| 96 | 4-chloro | 4-chlorophenyl | morpholino | 1 | 0 | 2 | 0 | 2 | 1 |
| 97 | 6-isopropyl | phenyl | morpholino | 1 | 0 | 0 | 2 | 2 | 1 |
| 98 | 6-n-butyl | phenyl | morpholino | 1 | 0 | 0 | 2 | 2 | 1 |

TABLE 3-continued

| No. | $(R^1)_m$ | $R^2$ | $-NR^3R^4$ | m | n | p | q | x | y |
|---|---|---|---|---|---|---|---|---|---|
| 99 | H | 4-isopropyl-phenyl | morpholino | 1 | 0 | 0 | 2 | 2 | 1 |
| 100 | H | 4-isoamyl-phenyl | morpholino | 1 | 0 | 0 | 2 | 2 | 1 |
| 101 | H | β-naphthyl | morpholino | 1 | 0 | 0 | 2 | 2 | 1 |
| 102 | H | 4-pyridyl | morpholino | 1 | 0 | 0 | 2 | 2 | 1 |

The compound of the invention was evaluated in urinating contraction of bladder by the following test method.

TEST METHOD

A male rat (Wistar strain) was fixed on his back under urethane anesthesia (1.5 g/kg, S.C.). A tracheal cannula was inserted into the rat to respire easily, and its hypogastrium was subjected to median dissection for exposing its bladder. A small opening was made on the top of the bladder to remove urine. To the bladder was inserted a polyethylene cannula. The bladder system was made to closed system by ligating urethra and ureter.

A physiological saline was injected into the bladder of rat at a rate of 0.05 mL/min. using a continuous injector so as to cause periodical urinating contraction. The intravesical pressure of the bladder was measured by means of a pressure transducer. The measured value was recorded on a pen-writing recorder. The compound to be tested was dissolved in a physiological saline and administered into the femoral vein using the polyethylene cannula.

METHOD OF EVALUATION

The action for relieving urinating contraction was evaluated by measuring a period of time during which the rhythmic bladder contraction was inhibited (period of contraction inhibition).

The compounds tested were those obtained in the working examples. The period of contraction inhibition measured on each compound is set forth in Table 4.

TABLE 4

| Compound | Mouse $LD_{50}$ (mg/kg/ i.v.) | Dose (mg/kg i.v.) | Number of Samples | Period of Contraction Inhibition(min.) |
|---|---|---|---|---|
| Control (Physi. Saline) | — | — | 6 | 1.6 |
| Example 20[A] | >120 | 12 | 6 | 9.7 |
| Example 20[B] | 140 | 6 | 2 | 0.4 |
| Example 20[C] | 180 | 6 | 2 | 6.0 |
| Example 24[A] | 62 | 12 | 8 | 5.6 |
| Example 24[B] | 32 | 6 | 2 | 8.5 |
| Example 24[C] | 167 | 6 | 2 | 0.7 |
| Example 21 | >100 | 10 | 1 | 7.0 |
| Example 26 | 37 | 4 | 2 | 7.3 |
| Example 10 | 3 | 8 | 2 | 14.5 |
| Example 11 | 37 | 8 | 4 | 3.9 |
| Example 12 | — | 8 | 2 | 2.5 |
| Example 1 | — | 1 | 3 | 2.8 |
| Example 14 | 17 | 8 | 3 | 12.7 |
| Example 15 | 23 | 8 | 3 | 4.7 |
| Example 3 | — | 8 | 2 | 2 |
| Example 2 | — | 8 | 2 | 16 |
| Example 13 | — | 8 | 2 | 18 |
| Example 16 | — | 8 | 3 | — |
| Example 31 | — | 8 | 3 | — |
| Example 32 | — | 8 | 3 | 6 |

TABLE 4-continued

| Compound | Mouse $LD_{50}$ (mg/kg/ i.v.) | Dose (mg/kg i.v.) | Number of Samples | Period of Contraction Inhibition(min.) |
|---|---|---|---|---|
| Example 34 | — | 8 | 2 | 3 |
| Example IX | 48 | 5 | 4 | 10.7 |
| Example XI | 170 | 17 | 2 | 6.0 |
| Example II | 47 | 5 | 10 | 3.8 |
| Example XII | >200 | 20 | 2 | 3.5 |

The results seen in Table 4 clearly indicate that the compound of the invention is effective in relieving urinating contraction. Further, the toxicity of the compound is set forth in Table 4 in terms of $LD_{50}$ (mg/kg) calculated by Probit method.

The alkylenediamine derivative or its pharmacologically acceptable salt according to the invention is useful as an active ingredient for a pharmaceutical for treatment of dysuria.

The pharmaceutical for treatment of dysuria according to the invention can be used either in a general preparation form for oral administration or in the form for parenteral adminstration such as injections and suppositories. Preparation forms for oral administration may be tablets, capsules, powder, granules, syrup and the like. Preparation forms for parenteral administration may be injections and suppositories and the like. For the formulation of these preparations, excipients, disintegrants, binders, lubricants, pigments, diluents and the like which are commonly employed in the art may be used. The excipients may include glucose, lactose and the like. Starch, carboxymethylcellulose calcium and the like may be used as the disintegrants. Magnesium stearate, talc and the like may be used as the lubricants. The binders may be hydroxypropylcellulose, gelatin, polyvinylpyrrolidone and the like.

The dose may usually be about 0.1 mg/day to 10.0 mg/day in the case of an injectable preparation and about 1.0 mg/day to 500 mg/day in the case of oral administration, both for adult. The dose may be either increased or decreased depending upon the age and conditions of patients.

The present invention is further described by the following examples.

EXAMPLE 1

2-[3-(4-Phenoxypiperidino)propyl]-2H-1,2-benzothiazin-4(3H)-one 1,1-dioxide Hydrochloride (1) 2-(3-Chloropropyl)-2H-1,2-benzothiazin-4(3H)-one 1,1-dioxide Ethylene Ketal In 1,2-dimethoxyethane (450 mL) was suspended 60% sodium hydride (2.0 g, 502 mmol.), and then 2H-1,2-benzothiazin-4(3H)-one 1,1-dioxide ethylene ketal (12.06 g, 50 mmol.) was added to the suspension. The suspension was heated to 100° C. for 1 hour under stirring. The reaction liquid was cooled to 50° C., and to this was added a solution of 1-bromo-3-chloropropane (23.62 g, 150 mmol.) in 1,2-dimethoxyethane (50 mL). The mixture was heated to 100° C. for 21 hours under refluxing. The reaction liquid was filtered to remove insolubles and the solvent was evaporated to give a residue. The residue was treated with water and ether, and the organic layer was taken out. The organic solution was washed with water and a saturated aqueous sodium chloride solution, and dried over anhydrous sodium sulfate. The solvent was evaporated to leave the desired compound (8.89 g, yield 56%) as a yellow oil.

$^1$H-NMR (CDCl$_3$) δ: 2.0–2.1 (2H, m), 3.62 (2H, t, J=6 Hz), 3.71 (2H, t, J=6 Hz), 3.91 (2H, s), 4.1–4.2 (2H, m), 4.2–4.3 (2H, m), 7.4–7.6 (3H, m), 7.7–7.8 (1H, m).

(2) 2-[3-(4-Phenoxypiperidino)propyl]-2H-1,2-benzothiazin-4(3H)-one 1,1-Dioxide Ethylene Ketal In dichloromethane (1 mL) were dissolved 2-(3-chloropropyl)-2H-1,2-benzothiazin-4(3H)-one 1,1-dioxide ethylene ketal (830 mg, 2.6 mmol.) obtained in (1) and 4-phenoxypiperidine (500 mg, 2.6 mmol.). From the solution was distilled off dichloromethane, and the residue was heated to 110° C. for 5.5 hours under stirring and in nitrogen atmosphere. To the reaction liquid were added an aqueous saturated sodium hydrogen carbonate solution and ethyl acetate, and the organic layer was taken out. The organic solution was washed with water and an aqueous saturated sodium chloride solution, and then dried over anhydrous sodium sulfate. The solvent was distilled off to leave a residue. The residue was treated by silica gel column chromatography (chloroform/methanol=40/1) to obtain the desired compound (700 mg, yield 58%) as a yellow oil.

$^1$H-NMR (CDCl$_3$) δ: 1.7–1.9 (4H, m), 1.9–2.1 (2H, m), 2.2–2.3 (2H, m), 2.4–2.5 (2H, m), 2.7–2.8 (2H, m), 3.5–3.6 (2H, m), 3.91 (2H, s), 4.1–4.2 (2H, m), 4.3–4.4 (3H, m), 6.9–7.0 (3H, m), 7.2–7.3 (2H, m), 7.5–7.6 (3H, m), 7.75–7.8 (1H, m).

(3) 2-[3-(4-Phenoxypiperidino)propyl]-2H-1,2-benzothiazin-4(3H)-one 1,1-Dioxide Hydrochloride In methanol (10 mL) was dissolved 2-[3-(4-phenoxypiperidino)propyl]-2H-1,2-benzothiazon-4(3H)-one 1,2-dioxide ethylene ketal (700 mg, 1.5 mmol.) obtained in (2). To the obtained solution was added 3N hydrochloric acid (10 mL), and the mixture was heated under refluxing for 15 min. The solvent was distilled off from the reaction liquid. To the residue was added water, and the mixture was kept in a cooled place. Crude crystals deposited were collected by filtration, and recrystallized from dichloromethane/methyl ethyl ketone to give the desired compound (440 mg, yield 64%) as a white crystalline product.

M.P.: 204°–207° C., IR (KBr) cm$^{-1}$: 3400, 2500, 1700, 1600, 1590, 1490, 1340, 1240, 1230, 1170, 1120, 1110, 1050, 975, 780, 750, 690, 570. $^1$H-NMR (CDCl$_3$) δ: 2.1–2.3 (4H, m), 2.5–2.7 (2H, m), 3.0–3.2 (4H, m), 3.3–3.4 (2H, m), 3.4–3.5 (2H, m), 4.50 (2H, s), 4.6–4.7 (1H, m), 6.9–7.0 (3H, m), 7.2–7.3 (2H, m), 7.7–7.9 (3H, m), 8.0–8.1 (1H, m).

EXAMPLE 2

2-[3-(4-Benzyloxypiperidino)propyl]-2H-1,2-benzothiazin-4(3H)-one 1,1-Dioxide Hydrochloride (1) 2-[3-(4-Benzyloxypiperidino)propyl]-2H-1,2-benzothiazin-4(3H)-one 1,1-Dioxide Free Base In 1,2-dimethoxyethane (40 mL) was suspended 60% sodium hydride (180 mg, 4.5 mmol.), and then 2H-1,2-benzothiazin-4(3H)-one 1,1-dioxide ethylene ketal (1.00 g, 4.1 mmol.) was added to the suspension. The suspension was heated for 1 hour under stirring. The reaction liquid was cooled to 50° C., and to this was added a solution of 4-benzyloxy-1-(3-chloropropyl)piperidine (1.11 g, 4.1 mmol.) in 1,2-dimethoxyethane (10 mL). The mixture was further heated for 20 hours under refluxing. The reaction liquid was filtered to remove insolubles and the solvent was distilled off to give a residue. To the residue were added aqueous 9% hydrochloric acid (30 mL) and methanol (30 mL), and the mixture was heated for 15 min. under refluxing. The reaction liquid was placed under reduced pressure to distill methanol off. The residue was treated with ice-water, and the deposited oil was extracted with dichloromethane. The dichloromethane portion was washed with water and an aqueous saturated sodium chloride solution, and dried over anhydrous sodium sulfate. The solvent was distilled off to leave a residue. The residue was treated by silica gel column chromatography (chloroform/methanol=30/1) to give the desired compound (860 mg, yield 45%) as a red oil.

$^1$H-NMR (CDCl$_3$) δ: 1.6–2.8 (12H, m), 3.2–3.3 (2H, m), 3.4–3.5 (1H, m), 4.46 (2H, s), 4.53 (2H, s), 7.2–8.1 (9H, m).

(2) 2-[3-(4-Benzyloxypiperidino)propyl]-2H-1,2-benzothiazin-4(3H)-one 1,1-Dioxide Hydrochloride In methanol (1 mL) was dissolved 2-[3-(4-benzyloxypiperidino)propyl]-2H-1,2-benzothiazin-4(3H)-one 1,1-dioxide free base (860 mg, 2 mmol.) obtained in (1). To the resulting solution was added aquoeus 9% hydrochloric acid (1 mL), and the mixture was placed under reduced pressure to distill the solvent off. The residue was then treated with water and dried to give the desired compound (700 mg, yield 36%) as an orange amorphous product.

IR (KBr) cm$^{-1}$: 3400, 2925, 1690, 1580, 1445, 1335, 1270, 1220, 1170, 1120, 1050, 910, 750, 700, 570. $^1$H-NMR (CDCl$_3$) δ: 1.7–2.2 (6H, m), 2.8–3.8 (9H, m), 4.4–4.6 (4H, m), 7.2–8.0 (9H, m).

EXAMPLE 3

3-[3-(4-Benzylpiperidino)propyl]-1H-2,3-benzothiazin-4(3H)-one 2,2-Dioxide Fumarate (1) 3-[3-(4-Benzylpiperidino)propyl]-1H-2,3-benzothiazin-4(3)-one 2,2-Dioxide Free Base In dry ethanol was dissolved metallic sodium (120 mg, 5.1 mmol.). To the solution was added 1H-2,3-benzothiazin-4(3H)-one 2,2-dioxide (1.0 g, 5.1 mmol.), and the mixture was heated for one hour under refluxing. To the reaction liquid were added 4-benzyl-1-(3-chloropropyl)piperidine (1.28 g, 5.1 mol.) and dry ethanol (10 mL), and subsequently the mixture was heated under refluxing for 6 hours. The reaction liquid was placed under reduced pressure to distill the solvent off. The resulting residue was treated with water, and extracted with ethyl acetate. The ethyl acetate portion was washed with water and an aqueous saturated sodium chloride solution, and dried over anhydrous sodium sulfate. The dried solution was placed under reduced pressure to distill the solvent off, and the resulting resiude was treated by silica gel column chromatography (ethyl acetate/hexane=2/1) to give the desired compound (860 mg, yield 40%) as a yellow oil.

$^1$H-NMR (CDCl$_3$) δ: 1.2–1.3 (2H, m), 1.4–1.7 (3H, m), 1.8–2.0 (4H, m), 2.3–2.5 (4H, m), 2.89 (2H, d, J=11 Hz), 3.9–4.0 (2H, m), 4.58 (2H, s), 7.0–7.4 (6H, m), 7.5–7.6 (2H, m), 8.21 (1H, d, J=8 Hz).

(2) 3-[3-(4-Benzylpiperidino)propyl]-1H-2,3-benzothiazon-4(3H)-one 2,2-Dioxide Fumarate 3-[3-(4-Benzylpiperidino)propyl]-1H-2,3-benzothiazin-4(3H)-one 2,2-dioxide free base (840 mg, 2.0 mmol.) obtained in (1) was treated with fumaric acid (240 mg, 2.0 mmol.) in ethanol (10 mL), to give the desired compound (830 mg, yield 77%) as a crystalline powder.

M.p.: 154°–155° C., IR (KBr) cm$^{-1}$: 3400, 2925, 1680, 1600, 1450, 1430, 1350, 1310, 1285, 1195, 1170, 1140, 985, 750, 745, 650. $^1$H-NMR (DMSO-d$_6$) δ: 1.2–1.3 (2H, m), 1.5–1.6 (3H, m), 1.8–1.9 (2H, m), 2.1–2.2 (2H, m), 2.4–2.6 (4H, m), 3.00 (2H, d, J=11 Hz), 3.8–3.9 (2H, m), 5.22 (2H, s), 6.53 (2H, s), 7.1–7.3 (5H, m), 7.5–7.8 (3H, m, ArH), 8.05 (1H, d, J=8 Hz).

EXAMPLE 4

2-(3-Morpholino-1-phenylpropyl)-2H-1,2-benzothiazin-3(4H)-one 1,1-Dioxide Fumarate In toluene (7 mL) were suspended 2H-1,2-benzothiazin-3(4H)-one 1,1-dioxide (250 mg, 1.3 mmol.), 1-chloro-3-morpholino-1-phenylpropane (340 mg, 1.4 mmol.), potassium carbonate (250 mg, 1.8 mmol.) and a catalytic amount of cupper powder. The suspension was heated for 12 hours under refluxing. The reaction liquid was cooled, and the insolubles were filtered off. The solvent was distilled off to leave a residue. To the residue were added water and ethyl acetate, and the organic layer was taken out. The organic solution was washed with water and an aqueous saturated sodium chloride solution, and dried over anhydrous sodium sulfate. The solvent was distilled off, and the resulting residue was treated by silica gel column chromatogrpahy (ethyl acetate) to give the free base of the desired compound (180 mg) as an oil. The free base was treated in the conventional manner to convert into the desired fumarate.

M.p.: 186°–187° C., IR (KBr) cm$^{-1}$: 3400, 1710, 1570, 1450, 1340, 1255, 1185, 1130, 1090, 1070, 990, 925, 875, 750, 720, 690, 620, 570. $^1$H-NMR (CD$_3$OD) δ: 2.4–3.0 (8H, m), 3.6–3.9 (4H, m), 5.6–5.9 (1H, m), 6.73 (2H, s), 7.1–7.9 (9H, m).

EXAMPLE 5

3-(3-Morpholino-1-phenylpropyl)-2H-1,3-benzothiazin-4(3H)-one 1,1-Dioxide Fumarate In methyl ethyl ketone (5 mL) were suspended 2H-1,3-benzothiazin-4(3H)-one 1,1-dioxide (100 mg, 0.518 mmol.), 1-chloro-3-morpholino-1-phenylpropane (130 mg, 0.54 mmol.), and potassium carbonate (180 mg, 1.3 mmol.). The suspension was heated overnight under refluxing. The reaction liquid was cooled, and the insolubles were filtered off. The solvent was distilled off to give a residue. To the residue were added water and ethyl acetate, and the organic layer was taken out. The organic solution was washed with water and an aqueous saturated sodium chloride solution, and dried over anhydrous sodium sulfate. The solvent was distilled off, and the residue was treated by silica gel column chromatography (chloroform/methanol=50/1) to give the free base of the desired compound (70 mg, yield 35%) as an oil.

The free base was treated in the conventional manner to convert into the desired fumarate.

M.p.: 218° C. (decomp.), IR (KBr) cm$^{-1}$: 3400, 1680, 1650, 1440, 1420, 1390, 1320, 1270, 1160, 1125, 1110, 1085, 970, 900, 800, 750, 695, 680, 530. $^1$H-NMR (CD$_3$OD) δ: 2.3–2.5 (2H, m), 2.5–3.3 (6H, m), 3.7–3.9 (4H, m), 4.58 (1H, d, J=16 Hz), 4.88 (1H, d, J=16 Hz), 6.1–6.3 (1H, m), 6.70 (2H, s), 7.3–8.4 (9H, m).

EXAMPLES 6 AND 7

3-(2-Hydroxy-3-morpholinopropyl)-1H-2,3-benzothiazin-4(3H)-one 2,2-Dioxide ½ Fumarate—Example 6

3-(2-Ethoxy-3-morpholinopropyl)-1H-2,3-benzothiazin-4(3H)-one 2,2-Dioxide Fumarate—Example 7

(1) In dry ethanol (10 mL) was dissolved metallic sodium (23 mg, 1 mmol.), and to the solution was added 1H-2,3-benzothiazin-4(3H)-one 2,2-dioxide (197 mg, 1 mmol.). The mixture was stirred at 50° C. for 30 min. To the reaction solution was added 1-chloro-3-morpholino-2-propanol (198 mg, 1.1 mmol.). The mixture was then heated for 6 hours under refluxing. The reaction liquid was placed under reduced pressure to distill the solvent off. The resulting residue was treated with 1N hydrochloric acid and ethyl acetate. The aqueous layer was taken out, and made basic by addition of potassium carbonate. The oil precipitated and was extracted with ethyl acetate. The ethyl acetate portion was washed with an aqueous saturated sodium chloride solution, and then dried over anhydrous sodium sulfate. The dried ethyl acetate portion was placed under reduced pressure to distill the solvent off. The resulting residue was treated by silica gel column chromatography (chloroform/methanol=40/1) to give 3-(2-hydroxy-3-morpholinopropyl)-1H-2,3-benzothiazin-4(3H)-one 2,2-dioxide (215 mg, yield 63%) as a colorless oil, and 3-(2-ethoxy3-morpholinopropyl)-1H-2,3-benzothiazin-4(3H)-one 2,2-dioxide (70 mg, yield 20%) as an colorless oil.

3-(2-Hydroxy-3-morpholinopropyl)-1H-2,3-benzothiazin-4(3H)-one 2,2-Dioxide

IR (KBr) cm$^{-1}$: 3400, 2950, 2910, 2850, 2810, 1680, 1600, 1450, 1350, 1305, 1280, 1240, 1195, 1160, 1140, 1115, 1010, 865, 750. $^1$H-NMR (CDCl$_3$) δ: 2.3–2.7 (6H, m), 3.40 (1H, bs), 3.6–3.8 (4H, m), 4.0–4.2 (3H, m), 4.64 (1H, d, J=16 Hz), 4.69 (1H, d, J=16 Hz), 7.33 (1H, d, J=8 Hz), 7.5–7.7 (2H, m), 8.18 (1H, d, J=8 Hz).

3-(2-Ethoxy-3-morpholinopropyl)-1H-2,3-benzothiazin-4(3H)-one 2,2-Dioxide

IR (KBr) cm$^{-1}$: 2930, 2850, 2800, 1700, 1440, 1405, 1360, 1320, 1295, 1260, 1110, 1070, 1000, 860. $^1$H-NMR (CDCl$_3$) δ: 1.41 (3H, t, J=7 Hz), 2.2–2.6 (6H, m), 2.84 (1H, dd, J=6 Hz, 14 Hz), 3.04 (1H, dd, J=2 Hz, 13 Hz), 3.6–3.8 (5H, m), 4.39 (2H, q, J=7 Hz), 4.92 (1H, d, J=13 Hz), 4.96 (1H, d, J=13 Hz), 7.4–7.5 (1H, m), 7.5–7.6 (2H, m), 7.98 (1H, d, J=8 Hz).

(2) 3-(2-Hydroxy-3-Morpholinopropyl)-1H-2,3-benzothiazin-4(3H)-one 2,2-Dioxide ½ Fumarate (Example 6)

To ethanol (4 mL) were added 3-(2-hydroxy-3-morpholinopropyl)-1H-2,3-benzothiazin-4(3H)-one 2,2-dioxide (215 mg, 0.63 mmol.) and fumaric acid. (73 mg, 0.63 mmol.). The mixture was heated to give a solution. The solution was kept at room temperature. Crystals precipitated and were collected by filtration, to give the desired compound (187 mg, yield 75%) as a white crystalline product.

M.p.: 175°–177° C., IR (KBr) cm$^{-1}$: 3370, 1690, 1575, 1340, 1285, 1255, 1175, 1135, 980. $^1$H-NMR (D$_2$O) δ:

3.2–3.5 (6H, m), 3.9–4.2 (6H, m), 4.4–4.5 (1H, m), 5.07 (2H, s), 6.52 (1H, s), 7.54 (1H, d, J=8 Hz), 7.67 (1H, dd, J=7 Hz, 8 Hz), 7.79 (1H, dd, J=7 Hz, 8 Hz), 8.15 (1H, d, J=8 Hz).

(3) 3-(2-Ethoxy-3-morpholinopropyl)-1H-2,3-benzothiazin-4(3H)-one 2,2-Dioxide ½ Fumarate (Example 7)

To ethanol (2 mL) were added 3-(2-ethoxy-3-morpholinopropyl)-1H-2,3-benzothiazin-4(3H)-one 2,2-dioxide (73 mg, 0.2 mmol.) and fumaric acid (23 mg, 0.2 mmol.). The mixture was heated to give a solution. The solution was kept at room temperature. Crystals precipitated and were collected by filtration, to give the desired compound (64 mg, yield 65%) as a white crystalline product.

M.p.: 128°–129° C., IR (KBr) cm$^{-1}$: 3400, 1710, 1320, 1300, 1265, 1130, 1080, 985, 645. $^1$H-NMR (CD$_3$OD) δ: 1.40 (3H, t, J=7 Hz), 2.7–3.1 (18H, m), 3.7–3.9 (4H, m), 3.9–4.0 (1H, m), 4.38 (2H, q, J=7 Hz), 4.98 (2H, s), 6.72 (2H, s), 7.4–7.6 (3H, m), 7.95 (1H, d, J=8 Hz).

EXAMPLE 8

2-(2-Hydroxy-3-morpholinopropyl)-2H-1,2-benzothiazin-4(3H)-one 1,1-Dioxide ½ fumarate (1) 2-(2-Hydroxy-3-morpholinopropyl)-2H-1,2-benzothiazin-4(3H)-one 1,1-Dioxide Ethylene Ketal A suspension of 2H-1,2-benzothiazin-4(3H)-one 1,1-dioxide ethylene ketal (0.48 g, 2 mmol) and 60% sodium hydride (0.08 g, 2 mmol.) in 1,2-dimethoxyethane (20 mL) was heated for one hour under refluxing. The resulting reaction liquid was further heated for 16 hours under refluxing, after addition of 1-chloro-3-morpholino-2-propanol (0.36 g, 2 mmol.). The reaction liquid was placed under reduced pressure to distill the solvent off. The residue was treated with 1N hydrochloric acid and ethyl acetate, and the aqueous layer was taken out. The aquous solution was made basic by addition of potassium carbonate, and the precipitated oil was extracted with ethyl acetate. The extract solution was washed with an aqueous saturated sodium chloride solution, and dried over anhydrous sodium sulfate. The dried solution was placed under reduced pressure to distill the solvent off. The resulting residue was treated by silica gel column chromatography (ethyl acetate/methanol= 10/1) to give the desired compound (0.54 g, yield 70%) as a colorless oil.

IR (KBr) cm$^{-1}$: 3420, 2890, 2810, 1440, 1320, 1270, 1240, 1150, 1110, 1050, 1010, 975, 950, 865, 760, 690. $^1$H-NMR (CDCl$_3$) δ: 2.4–2.7 (6H, m), 3.45 (1H, dd, J=6 Hz, 15 Hz), 3.6–3.8 (5H, m), 3.9–4.0 (1H, m), 4.08 (2H, s), 4.1–4.3 (4H, m), 7.4–7.6 (3H, m), 7.77 (1H, d, J=8 Hz).

(2) 2-(2-Hydroxy-3-morpholinopropyl)-2H-1,2-benzothiazin-4(3H)-one 1,1-Dioxide

In a mixture of methanol (4 mL) and 9% hydrochloric acid (4 mL) was dissolved 2-(2-hydroxy-3-morpholinopropyl)-2H-1,2-benzothiazin-4(3H)-one 1,1-dioxide ethylene ketal (0.38 g, 1 mmol.) obtained in (1). The mixture was then heated for 30 min. under refluxing. The reaction liquid was placed under reduced pressure to distill the solvent off. The residue was treated with an aqueous saturated sodium hydrogen carbonate solution and ethyl acetate. The organic layer was taken out. The organic solution was washed with water and then an aqueous saturated sodium chloride solution, and dried over anhydrous sodium sulfate. The dried solution was placed under reduced pressure to distill the solvent off, to obtain the desired compound (0.33 g, yield 97%) as a yellow oil.

IR (KBr) cm$^{-1}$: 3400, 2920, 2850, 2800, 1695, 1580, 1440, 1330, 1275, 1230, 1170, 1110, 1065, 1045, 1005, 920, 860, 760. $^1$H-NMR (CDCl$_3$) δ: 2.3–2.7 (6H, m), 3.13 (1H, dd, J=6 Hz, 14 Hz), 3.3 (1H, bs), 3.45 (1H, dd, J=2 Hz, 14 Hz), 3.6–3.8 (4H, m), 3.8–4.0 (1H, m), 4.63 (1H, d, J=18 Hz), 4.71 (1H, d, J=18 Hz), 7.7–7.8 (2H, m), 7.85 (1H, d, J=8 Hz), 8.08 (1H, d, J=8 Hz).

(3) 2-(2-Hydroxy-3-morpholinopropyl)-2H-1,2-benzothiazin-4(3H)-one 1,1-Dioxide ½ Fumarate In ethanol (6 mL) were dissolved under heating 2-(2-hydroxy-3-morpholinopropyl)-2H-1,2-benzothiazin-4(3H)-one 1,1-dioxide (0.33 g, 0.97 mmol.) obtained in (2) and fumaric acid (0.11 g, 0.97 mmol.). The solution was kept at room temperature. Crystals precipitated and were collected by filtration, to give the desired compound (0.34 g, yield 65%) as a white crystalline product.

M.p.: 128°–129° C., IR (KBr) cm$^{-1}$: 3550, 3450, 1700, 1580, 1560, 1440, 1340, 1320, 1275, 1175, 1150, 1135, 1110, 980, 915, 780, 760, 655, 580. $^1$H-NMR (CD$_3$OD) δ: 2.5–2.8 (6H, m), 3.17 (1H, dd, J=7 Hz, 14 Hz), 3.6–3.8 (4H, m), 3.9–4.1 (1H, m), 6.71 (1H, s), 7.7–8.0 (3H, m), 8.07 (1H, d, J=8 Hz).

EXAMPLE 9

3-(3-Morpholino-3-phenylpropyl)-1H-2,3-benzothiazin-4(3H)-one 2,2-Dioxide ½ Fumarate (1) 3-(3-Oxo-3-phenylpropyl)-1H-2,3-benzothiazin-4(3H)-one 2,2-Dioxide 1H-2,3-Benzothiazin-4(3H)-one 2,2-dioxide (1 g, 5.08 mmol.) was added to a solution of powdery potassium hydroxide (334 mg, 5.08 mmol.) in methanol (4 mL). The mixture was then stirred at room temperature for 15 min. The solution was placed under reduced pressure to distill the solvent off to dryness. To the dried product were added 3-chloropropiophenone (856 mg, 5.08 mmol.) and dimethylformamide (8 mL). The mixture was heated to 120° C. for 6 hours under stirring. The reaction liquid was placed under reduced pressure to distill the solvent off. To the resulting residue was added water, and it was extracted with ethyl acetate. The extract solution was washed with an aqueous saturated sodium chloride solution, and dried over anhydrous sodium sulfate. The dried extract solution was placed under reduced pressure to distill the solvent off. The resulting oil was treated by silica gel column chromatography (chloroform) to give the desired compound (1.13 g, yield 68%) as a white solid.

$^1$H-NMR (CDCl$_3$) δ: 3.4–3.6 (2H, m), 4.4–4.5 (2H, m), 4.63 (2H, s), 7.3–8.3 (9H, m).

(2) 2-(2-Hydroxy-3-phenylpropyl)-1H-2,3-benzothiazin-4(3H)-one 2,2-Dioxide

To a suspension of 3-(3-oxo-3-phenylpropyl)-1H-2,3-benzothiazin-4(3H)-one 2,2-dioxide (880 mg, 2.67 mmol.) obtained in (1) in methanol (35 mL) was added under cooling with ice-water sodium borohydride (310 mg, 8.16 mmol.). The mixture was stirred for 40 min. under the same cooling. The excessive sodium borohydride in the reaction liquid was decomposed by acetic acid (500 mg), and the liquid was placed under reduced pressure to distill the solvent off. The residue was extracted with ethyl acetate after addition of water. The extract solution was washed with an aqueous saturated sodium chloride solution, and dried over anhydrous sodium sulfate. The dried extract portion was placed under reduced pressure to distill the solvent off, to give the desired compound (1.02 g) as a yellow oil.

$^1$H-NMR (CDCl$_3$) δ: 2.1–2.3 (2H, m), 4.1–4.3 (2H, m), 4.56 (2H, s), 4.7–4.9 (1H, m), 7.3–8.3 (9H, m).

(3) 2-(2-Chloro-3-phenylpropyl)-1H-2,3-benzothiazin-4(3H)-one 2,2-Dioxide

In dichloromethane (2 mL) was dissoloved 3-(3-hydroxy-3-phenylpropyl)-1H-2,3-benzothiazin-4(3H)-one 2,2-dioxide (1.02 g, 3.08 mmol.) obtained in (2). To the solution was dropwise added under ice-cooling a solution of thionyl chloride (420 mg, 3.53 mmol.) in dichloromethane (2 mL). The mixture was stirred at room temperature for 15 hours. To th reaction liquid was added under ice-cooling an aqeous saturated sodium hydrogen carbonate solution, and the mixture was extracted with dichloromethane. The extract portion was washed with an aqeuous saturated sodium chloride solution, and dried over anhydrous sodium sulfate. The dried extract portion was placed under reduced pressure to distill the solvent off. The obtained crude product was treated by silica gel column chromatography (ethyl acetate/n-hexane=1/3) to give the desired compound (690 mg, yield 64%) as a colorless oil.

$^1$H-NMR (CDCl$_3$) δ: 2.5–2.7 (2H, m), 4.1–4.3 (2H, m), 4.53 (2H, s), 5.0–5.1 (1H, m), 7.3–8.3 (9H, m).

(4) 3-(3-Morpholino-3-phenylpropyl)-1H-2,3-benzothizin-4(3H)-one 2,2-Dioxide ½ Fumarate A mixture of 2-(2-chloro-3-phenylpropyl)-1H-2,3-benzothiazin-4(3H)-one 2,2-dioxide (680 mg, 1.95 mmol.) obtained in (3) and morpholine (500 mg, 5.75 mmol.) was heated to 110° C. for 6 hours under stirring. The reaction liquid was extracted with ethyl acetate after addition of an aqueous saturated sodium hydrogen carbonate solution. The extract portion was washed with an aqueous saturated sodium chloride solution, and dried over anhydrous sodium sulfate. The dried extract portion was placed under reduced pressure to distill the solvent off. Thus obtained crude product was subjected to silica gel column chromatography (ethyl acetate/n-hexane=1/1) to give the free base of the desired compound (698 mg, yield 89.4%). The free base was warmed to 50° C. after addition of fumaric acid (200 mg, 1.74 mmol.) and ethanol (7 mL) to give a homogeneous solution. The solution was then stirred overnight at room temperature. Crystals precipitated and were collected by filtration. The collected crystals were dried at 50° C. under reduced pressure to give the desired compound (606 mg, yield 76%) as a white crystalline product.

M.p.: 130° C., IR (Kr) cm$^{-1}$: 3400, 2950, 1670, 1590, 1450, 1330, 1300, 1280, 1235, 1190, 1160, 1155, 1100, 1060, 980, 910, 810, 790, 730, 690, 550. $^1$H NMR (CD$_3$OD) δ: 2.2–2.7 (6H, m), 3.4–3.6 (5H, m), 3.6–4.0 (2H, m), 4.82 (2H, 9), 6.72 (2H, 0), 7.3–8.2 (9H, m).

In the following Examples 10 to 16, the compounds were prepared essentially in the same manner as in Example 1. The prepared compounds and characteristics thereof are set forth below.

Example 10

2-[3-(4-Benzylpiperidino)propyl)-2H-1,2-benzothiazin-4(3H)-one 1,1-Dioxide Hydrochloride White crystalline product IR (KBr) cm$^{-1}$: 3455, 2925, 2650, 1700, 1590, 1450, 1340, 1230, 1170, 1160, 1120, 950, 920, 790, 770, 750, 700, 580. $^1$H-NMR (DMSO-d$_6$) δ: 1.6–1.8 (3H, m), 1.9–2.1 (2H, m), 2.2–2.3 (2H, m), 2.5–2.7 (4H, m), 3.0–3.6 (6H, m), 4.49 (2H, s), 7.0–8.1 (9H, m).

Example 11

2-[3-(N-Benzyl-N-butylamino)propyl]-2H-1,2-benzothiazin-4(3H)-one 1,1-Dioxide Hydrochloride Amorphous product IR (KBr) cm$^{-1}$:3370, 2930, 2850, 1690, 1580, 1450, 1340, 1270, 1220, 1170, 1120, 1040, 760, 740, 690, 570. $^1$H-NMR (CD$_3$OD) δ: 0.97 (3H, t, J=6 Hz), 1.38 (2H, m), 1.75 (2H, m), 1.9–2.4 (2H, m), 2.9–3.4 (6H, m), 4.3–4.6 (4H, m), 7.4–7.7 (5H, m), 7.7–8.0 (3H, m), 8.07 (1H, d, J=8 Hz).

Example 12

2-[3-(4-Diphenylmethyl-1-piperazinyl)propyl]-2H-1,2-benzothiazin-4(3H)-one 1,1-Dioxide Hydrochloride Pale brown poder IR (KBr) cm$^{-1}$: 3510, 3430, 2810, 2420, 1690, 1580, 1445, 1340, 1275, 1170, 1120, 760, 740, 710. $^1$H-NMR (CDCl$_3$) δ: 1.65 (2H, m), 2.2–2.4 (2H, m), 2.7–3.2 (6H, m), 3.30 (2H, t, J=6 Hz), 3.3–3.6 (2H, m), 4.38 (1H, s), 4.48 (2H, s), 7.2–7.4 (1OH, m), 7.7–7.9 (3H, m), 8.08 (1H, d, J=7 Hz), 12.68 (1H, bs).

Example 13

2-[2-(4-Benzylpiperidino)ethyl]-2H-1,2-benzothiazin-4(3H)-one 1,1-Dioxide Hydrochloride M.p.: 198°–201° C., IR (KBr) cm$^{-1}$: 3400, 1695, 1580, 1445, 1340, 1270, 1230, 1170, 1120, 1040, 760, 750, 700, 570. $^1$H-NMR (CD$_3$OD) δ: 1.5–1.6 (2H, m), 1.8–1.9 (3H, m), 2.5–2.6 (2H, m), 2.9–3.0 (2H, m), 3.3–3.4 (2H, m), 3.5–3.7 (4H, m), 4.5–4.6 (1H, m), 4.7–4.8 (1H, m), 7.1–7.3 (5H, m), 7.8–7.9 (3H, m), 8.0–8.1 (1H, m).

Example 14

2-[3-(4-Benzyl-1-piperazinyl)propyl]-2H-1,2-benzothiazin-4(3H)-one 1,1-Dioxide Hydrochloride M.p.: 235°–237° C. (decomp.), IR (KBr) cm$^{-1}$: 3400, 2350, 1690, 1580, 1440, 1345, 1270, 1230, 1170, 950, 780, 750, 695, 570. $^1$H-NMR (D$_2$O) δ: 2.0–2.1 (2H, m), 3.2–3.6 (14H, m), 4.35 (2H, s), 7.4–8.1 (9H, m).

Example 15

2-[3-[2-(1,2,3,4-Tetrahydroisoquinolyl)]propyl]-2H-1,2-benzothiazin-4(3H)-one 1,1-Dioxide Hydrochloride M.p.: 195°–203° C. (decomp.), IR (KBr) cm$^{-1}$: 3400, 2450, 2400, 1690, 1590, 1450, 1340, 1270, 1230, 1170, 1120, 1040, 900, 755, 570. $^1$H-NMR (D$_2$O) δ: 2.0–2.2 (2H, m), 2.9–3.4 (6H, m), 3.55–3.7 (2H, m), 4.1–4.6 (2H, m), 4.60 (2H, s), 7.1–8.0 (9H, m).

Example 16

2-[3-[4-(4-Methoxybenzyl)piperidino]propyl]-2H-1,2-benzothiazin-4(3H)-one 1,1-Dioxide Hydrochloride Amorphous product IR (KBr) cm$^{-1}$: 3400, 2925, 2500, 1700, 1610, 1590, 1510, 1445, 1340, 1245, 1170, 1130, 1030, 955, 920, 850, 770, 630, 580. $^1$H-NMR (D$_2$O) δ: 1.65–1.75 (1H, m), 1.8–1.9 (2H, m), 2.3–2.4 (2H, m), 2.56 (2H, d, J=7 Hz), 2.56–2.7 (2H, m), 3.31 (2H, t, J=6 Hz), 3.5–3.6 (2H, m), 3.78 (3H, s), 4.49 (2H, s), 6.8–8.1 (8H, m).

In the following Examples 17 to 22, the compounds were prepared essentially in the same manner as in Example 2. The prepared compounds and characteristics thereof are set forth below.

Example 17

2-(3-Morpholinopropyl)-2H-1,2-benzothiazin-4(3H)-one 1,1-Dioxide Fumarate

IR (KBr) cm$^{-1}$: 3400, 1690, 1540, 1170, 1120, 980, 770, 640, 570. $^1$H-NMR (CD$_3$OD) δ: 1.9–2.0 (2H, m), 2.8–3.0 (6H, m), 3.3–3.4 (4H, m), 3.9–4.0 (4H, m), 6.72 (2H, s), 7.8–8.1 (4H, m),

Example 18

2-(3-Diethylamino-1-phenylpropyl)-2H-1,2-benzothiazin-4(3H)-one 1,1-Dioxide Hydrochloride M.p.: 189°–191° C., IR (KBr) cm$^{-1}$: 3400, 2925, 2600, 2450, 1690, 1590, 1470, 1440, 1400, 1390, 1335, 1275, 1230, 1170, 1135, 1125, 1100, 1075, 1050, 1005, 890, 870, 845, 810, 750, 700, 635, 580, 550. $^1$H-NMR (CD$_3$OD) δ: 1.4–1.5 (6H, m), 2.2–3.4 (8H, m), 4.35 (1H, d, J=19 Hz), 4.66 (1H, d, J=19 Hz), 5.0–5.2 (1H, m), 6.8–7.8 (9H, m).

Example 19

2-(1-Phenyl-3-piperidinopropyl)-2H-1,2-benzothiazin-4(3H)-one 1,1-Dioxide Hydrochloride M.p.: 216°–221° C., IR (KBr) cm$^{-1}$: 3400, 2500, 1690, 1350, 1180, 710. $^1$H-NMR (CDCl$_3$) δ: 1.5–3.8 (14H, m), 4.1–4.8 (2H, m), 4.9–5.2 (1H, m), 6.8–7.8 (9H, m).

Example 20

(A) 2-(3-Morpholino-1-phenylpropyl)-2H-1,2-benzothiazin-4(3H)-one 1,1-Dioxide Hydrochloride M.p.: 220° C., IR (KBr) cm$^{-1}$: 3400, 2425, 1690, 1590, 1445, 1350, 1330, 1280, 1230, 1170, 1130, 1105, 1080, 1040, 1010, 980, 890, 760, 700, 640, 580, 550. $^1$H-NMR (CDCl$_3$) δ: 2.4–2.6 (1H, m), 2.8–3.6 (7H, m), 3.9–4.0 (2H, m), 4.2–4.3 (2H, m), 4.35 (1H, d, J=19 Hz), 4.66 (1H, d, J=19 Hz), 6.9–7.8 (9H, m).

(B) (−)-2-(3-Morpholino-1-phenylpropyl)-2H-1,2-benzothiazin-4(3H)-one 1,1-Dioxide Hydrochloride 2-(3-Morpholino-1-phenylpropyl)-2H-1,2-benzothiazin-4(3H)-one 1,1-dioxide hydrochloride (17.48 g, 40.0 mmol.) obtained in (A) was dissolved in an aqueous saturated sodium hydrogen carbonate solution (300 mL), and then extracted with ethyl acetate. The ethyl acetate portion was washed with water and an aqueous saturated sodium chloride solution, and dried over anhydrous sodium sulfate. The dried portion was placed under reduced pressure to distill the solvent off. To the obtained oil were added methanol (80 mL) and L-(+)-tartaric acid (6.00 g, 40.0 mmol.), and the mixture was warmed to 50° C. to give a homogenous solution. The solution was left to stand at room temperature for 5 hours. Crystals precipitated and was recrystallized twice from methanol to give a diastereomer (5.27 g, 47%) of an optical purity 93.2% e.e. in the form of a white powder. The product (5.26 g) was added to an aqueous saturated sodium hydrogen carbonate solution and extracted with ethyl acetate. The ethyl acetate portion was washed with an aqueous saturated sodium chloride solution, dried over anhydrous sodium sulfate, and placed under reduced pressure to distill the solvent off. To the residual oil were added ethnaol (20 mL) and then concentrated hydrochloric acid (1 mL). The mixture was allowed to stand overnight. Crystals precipitated and were collected by fitration. The collected crystals were washed with ethanol and placed under reduced pressure at 40° C. for 3 hours to dryness. Thus, there was obtained the desired compound (3.50 g, yield 20%) as a white crystalline product.

M.p.: 238°–240° C., [α]$^{23}$=−7.05° (c 0.1, methanol)

(C) (+)-2-(3-Morpholino-1-phenylpropyl)-2H-1,2-benzothiazin-4(3H)-one 1,1-Dioxide Hydrochloride To the mother liquer remaining after the recrystallization step in (B) was added an aqueous saturated sodium hydrogen carbonate solution, and it was extracted with ethyl acetate (100 mL). The ethyl acetate portion was washed with an aqueous saturated sodium chloride solution (200 mL), dried over anhydrous sodium sulfate, and placed under reduced pressure to distill the solvent off. To thus obtained amorphous product (12.0 g, 30.0 mmol.) were added methanol (50 mL) and D-(−)-tartaric acid (4.50 g, 30.0 mmol.), and the mixture was warmed to 50° C. to give a homogenous solution. The solution was allowed to stand overnight at room temperature. Crystals precipitated and were recrystallized twice from methanol to give a diastereomer (7.58 g, 69%) of an optical purity 100% e.e. in the form of a white powder. The product (7.58 g) was added to an aqueous saturated sodium hydrogen carbonate solution and extracted with ethyl acetate. The ethyl acetate portion was washed with an aqueous saturated sodium chloride solution, and dried over anhydrous sodium sulfate. The drying agent was filtered off. The filtrate was allowed to stand overnight at room temperature after addition of 4N hydrochloric acid gas/ethyl acetate (5 mL). Crystals precipitated and were collected by fitration. The collected crystals were washed with ethyl acetate, and placed under reduced pressure at 40° C. for 3 hours to dryness. Thus, there was obtained the desired compound (5.26 g, yield 30%) as a white crystalline product.

M.p.: 242°–244° C., [α]$^{23}$=+7.44° (c 0.1, methanol)

Example 21

2-(1-Phenyl-3-thiomorpholinopropyl)-2H-1,2-benzothiazin-4(3H)-one 1,1-Dioxide Hydrochloride M.p.: 224°–227° C., IR (KBr) cm$^{-1}$: 3410, 2400, 1690, 1340, 1170, 760. $^1$H-NMR (CD$_3$OD) δ: 2.3–4.0 (12H, m), 4.4–4.6 (2H, m), 5.0–5.3 (1H, m), 6.8–7.8 (9H, m).

Example 22

2-[3-Morpholino-1-(4-chlorophenyl)propyl]-2H-1,2-benzothiazin-4(3H)-one 1,1-Dioxide Hydrochloride M.p.: 254° C. (decomp.), IR (KBr) cm$^{-1}$: 3400, 2375, 1680, 1580, 1340, 1320, 1270, 1230, 1170, 1085, 1005, 890, 815, 740, 585, 550. $^1$H-NMR (CD$_3$OD) δ: 2.5–4.4 (14H, m), 5.2–5.4 (1H, m), 6.9–7.8 (8H, m).

In the following Examples 23 to 28, the compounds were prepared essentially in the same manner as in Example 3. The prepared compounds and characteristics thereof are set forth below.

Example 23

3-(1-Phenyl-3-piperidinopropyl)-1H-2,3-benzothiazin-4(3H)-one 2,2-Dioxide ½ Fumarate M.p.: 135°–137° C. (decomp.), IR (KBr) cm$^{-1}$: 2930, 1670, 1575, 1440, 1350, 1275, 1235, 1190, 1160, 1135, 990, 730. $^1$H-NMR (CDCl$_3$) δ: 1.4–2.0 (6H, m), 2.6–3.2 (8H, m), 4.99 (2H, s), 5.6–5.9 (1H, m), 6.63 (1H, s), 6.1–6.7 (8H, m), 6.9–7.1 (1H, m).

Example 24

(A) 3-(3-Morpholino-1-phenylpropyl)-1H-2,3-benzothiazin-4(3H)-one 2,2-Dioxide Fumarate M.p.: 144°–145° C., IR (KBr) cm$^{-1}$: 3400, 1680, 1450, 1345, 1270, 1170, 1130, 980, 910, 870, 800, 730, 690, 640, 560, 500. $^1$H-NMR (CD$_3$OD) δ: 2.3–3.1 (8H, m), 3.6–3.9 (4H, m), 4.96 (2H, s), 5.7–5.9 (1H, m), 6.64 (2H, s), 7.2–7.7 (8H, m, ArH), 7.9–8.1 (1H, m).

(B) (−)-3-(3-Morpholino-1-phenylpropyl)-1H-2,3-benzothiazin-4(3H)-one 2,2-Dioxide Fumarate Water (90 mL) was added to 2-(3-morpholino-1-phenylpropyl)-1H-2,3-benzo-thiazin-4(3H)-one 2,2-dioxide fumarate (11.33 g, 28.3 mmol.) obtained in (A) as intermediate and D-(−)-tartaric acid (4.24 g, 28.2 mmol.), and the mixture was warmed to 80° C. to give a homogenous solution. The solution was left to stand overnight at room temperature. Crystals precipitated and were recrystallized three times from water to give a diastereomer (3.93 g, 25.2%) of an optical purity 98.7% e.e. in the form of a white powder. To the product (3.93 g) were added water (100 mL) and 28% aqueous ammonia (3 mL). The mixture was extracted with two portions of dichloromethane (50 mL). The dichloromethane extract was washed with an aqueous saturated sodium chloride solution, dried over anhydrous sodium sulfate, and placed under reduced pressure to distill the solvent off. To the residual amorphous product (2.34 g, 5.84 mmol.) was added ethnaol (30 mL). To this mixture was further added a solution of fumaric acid (678 mg, 5.84 mmol.) in ethnaol (20 mL). The resulting mixture was then stirred overnight. Crystals precipitated and were collected by fitration. The collected crystals were dried at 50° C. for 20 hour. Thus, there was obtained the desired compound (2.6 g, yield 18%) as a white crystalline product.

M.p.: 160°–163° C., [α]$^{23}$=−4.50° (c 0.2, methanol)

(C) (+)-3-(3-Morpholino-1-phenylpropyl)-1H-2,3-benzothiazin-4(3H)-one 2,2-Dioxide Fumarate To the mother liquer remaining after the recrystallization step in (B) was added 28% aqueous ammonia, and it was extracted with three portions of dichloromethane (100 mL). The dichloromethane extract was washed with an aqueous saturated sodium chloride solution (200 mL), dried over anhydrous sodium sulfate, and placed under reduced pressure to distill the solvent off. To thus obtained amorphous product (8.5 g, 21.2 mmol.) was added L-(+)-tartaric acid (3.18 g, 22.1 mmol.), and the mixture was warmed to 80° C. to give a homogenous solution. The solution was allowed to stand overnight at room temperature. Crystals precipitated and were recrystallized three times from water to give a diastereomer (3.32 g, 21.3%) of an optical purity 97.3% e.e. in the form of a white powder. To the product (3.32 g) were added water (100 mL) and 28% aqueous ammonia (3 mL), and the mixture was extracted with two portions of dichloromethane (50 mL). The dichloromethane extract was washed with an aqueous saturated sodium chloride solution (50 mL), dried over anhydrous sodium sulfate, and placed under reduced pressure to distill the solvent off. To the resulting amorphous product (2.38 g, 5.94 mmol.) was added ethanol (50 mL). To the mixture were further added a solution of fumaric acid (690 mg, 5.94 mmol.) in ethanol (20 mL). The mixture was stirred overnight at room temperature. Crystals precipitated and were collected by filtration. The collected crystals were dried at 50° C. for 20 hours. Thus, there was obtained the desired compound (2.35 g, yield 16%) as a white crystalline product.

M.p.: 163°–164° C., [α]$^{23}$=+4.3° (c 0.2, methanol)

Example 25

3-(3-Diethylamino-1-phenylpropyl)-1H-2,3-benzothiazin-4(3H)-one 2,2-Dioxide Fumarate M.p.: 169°–170° C., IR (KBr) cm$^{-1}$: 3400, 1680, 1590, 1540, 1440, 1340, 1270, 1230, 1190, 1160, 1140, 980, 800, 740, 720, 690, 640, 550, 500. $^1$H-NMR (CD$_3$OD) δ: 1.29 (6H, t, J=8 Hz), 2.6–2.8 (2H, m), 3.0–3.4 (6H, m), 5.10 (2H, s), 5.8–5.9 (1H, m), 6.70 (2H, s), 7.2–8.1 (9H, m).

Example 26

3-(1-Phenyl-3-thiomorpholinopropyl)-1H-2,3-benzothiazin-4(3H)-one 2,2-Dioxide Mesylate M.p.: 231°–233° C. (decomp.), IR (KBr) cm$^{-1}$: 1670, 1600, 1350, 1300, 1280, 1235, 1205, 1190, 1165, 1145, 1135, 1025, 960. $^1$H-NMR (CDCl$_3$/CD$_3$OD) δ: 2.5–4.2 (12H, m), 2.72 (3H, s), 4.82 (2H, bs), 5.7–5.9 (1H, m), 7.1–7.6 (8H, m), 7.9–8.1 (1H, m).

Example 27

3-[3-Morpholino-1-(4-chlorophenyl)propyl]-1H-2,3-benzothiazin-4(3H)-one 2,2-Dioxide Fumarate M.p.: 179° C., IR (KBr) cm$^{-1}$: 3425, 1680, 1350, 1270, 1160, 980, 730. $^1$H-NMR (CD$_3$OD) δ: 2.4–3.0 (8H, m), 3.6–3.8 (4H, m), 4.90 (2H, s), 6.68 (1H, s), 7.2–8.1 (8H, m).

Example 28

3-(3-Morpholino-2-phenylpropyl)-1H-2,3-benzothiazin-4(3H)-one 2,2-Dioxide Fumarate M.p.: 157°–158° C., IR (KBr) cm$^{-1}$: 3400, 2950, 1680, 1600, 1450, 1340, 1300, 1280, 1235, 1190, 1160, 1130, 1100, 980, 910, 870, 790, 730, 700, 680, 640, 550, 500. $^1$H-NMR (CD$_3$OD) δ: 2.6–2.8 (4H, m), 2.9–3.0 (1H, m), 3.0–3.1 (1H, m), 3.5–3.7 (5H, m), 4.0–4.1 (1H, m), 4.2–4.3 (1H, m), 4.6 (1H, d, J=6 Hz), 4.78 (1H, d, J=6 Hz), 6.71 (2H, s), 7.2–8.1 (9H, m).

Example 29

2-(3-Morpholino-3-phenylpropyl)-1H-1,2-benzothiazin-4(3H)-one 1,1-Dioxide Hydrochloride The above-mentioned compound was prepared essentially in the same manner as in Example 9.

M.p.: 214°–216° C. (decomp.), IR (KBr) cm$^{-1}$: 3550, 3380, 2580, 2550, 2470, 1695, 1455, 1340, 1280, 1170, 1125, 760, 700, 575. $^1$H-NMR (D$_2$O) δ: 2.5–2.7 (2H, m), 3.1–3.6 (6H, m), 3.8–4.1 (4H, m), 4.45 (1H, dd, J=4 Hz, 12 Hz), 7.5–7.6 (5H, m), 7.82 (1H, d, J=8 Hz), 7.92 (1H, dd, J=8 Hz, 8 Hz), 8.01 (1H, d, J=8 Hz).

Example 30

2-(3-Chloropropyl)-2H-1,2-benzothiazin-4(3H)-one 1,1-Dioxide

A mixture of 2-(3-chloropropyl)-2H-1,2-benzothiazin-4(3H)-one 1,1-dioxide ethylene ketal (5.0 g, 15.7 mmol.), 3N aqueous hydrochloric acid (30 mL) and methanol (30 mL) was heated under refluxing for 20 min. Methanol was distilled off under reduced pressure. To the residue was added water (30 mL), and the mixture was extracted with ethyl ether. The ethyl ether portion was washed with an aqueous saturated sodium chloride solution, dried over anhydrous sodium sulfate, and placed under reduced pressure to distill the solvent off, to give the desired compound (4.19 g, 100%) as a yellow oil.

$^1$H-NMR (CDCl$_3$) δ: 2.0–2.1 (2H, m), 3.36 (2H, t, J=6 Hz), 3.65 (2H, t, J=6 Hz), 4.46 (2H, s), 7.7–8.1 (4H, m).

Example 31

2-[3-(2,3-Dihydro-1H-benz[de]isoquinolin-2-yl)propyl]-2H-1,2-benzothiazin-4(3H)-one 1,1-Dioxide Hydrochloride A mixture of 2-(3-chloropropyl)-2H-1,2-benzothiazin-4(3H)-one 1,1-dioxide (324 mg, 1.18 mmol) obtained in Example 30, 3N aqueous hydrouchloric acid (30 mL) and methanol (30 mL) was heated to reflux for 20 min. The mixture was then placed under reduced pressure to distill methanol off. To the residue was added water, and the aqueous mixture was subjected to extraction with diethyl ether. The diethyl ether portion was washed with an aqueous saturated sodium chloride solution, dried over anhydrous sodium sulfate, and placed under reduced pressure to distill the solvent off. The resulting crude product was subjected to silica gel column chromatography. Its eluate at ethyl acetate/n-hexane (1/1) gave a red oil (200 mg, 41.7%). The oil was dissolved in methanol (1 mL), made acidic by 3N hydrochloric acid, and placed under reduced pressure to distill methanol off. The residue was allowed to stand after addition of water, to give the desired compound (133 mg, 61.0%) as an orange solid.

Free base $^1$H-NMR (CDCl$_3$) δ: 1.9–2.0 (2H, m), 2.70 (2H, t, J=7 Hz), 3.32 (2H, t, J=7 Hz), 3.95 (4H, s), 4.45 (2H, s), 7.1–8.1 (10H, m).

Hydrochloride (desired compound)

$^1$H-NMR (CD$_3$OD) δ: 2.2–2.3 (2H, m), 3.3–3.4 (2H, m), 3.4–3.5 (2H, m), 4.6–5.0 (6H, m), 7.5–8.1 (10H, m). IR (KBr) cm$^{-1}$: 3350, 1685, 1585, 1430, 1335, 1270, 1250, 1225, 1170, 1120, 1105, 1040, 990, 900, 820, 790, 770, 735, 680, 640, 570. M.p.: above 220° C. (decomp.).

Example 32

2-[3-(4-Cyano-4-phenylpiperidino)propyl]-2H-1,2-benzothiazin-4(3H)-one 1,1-Dioxide Fumarate 2-(3-Chloropropyl)-2H-1,2-benzothiazin-4(3H)-one 1,1-dioxide (485 mg, 1.77 mmol.) obtained in Example 30 and 4-cyano-4-phenylpiperidine (330 mg, 77 mmol.) were treated essentially in the same manner as in EXample 31 to give a free acid of the desired compound (411 mg, 56.7%) and its fumarate (300 mg, 56.9%).

Free base $^1$H-NMR (CDCl$_3$) δ: 1.75–1.85 (2H, m), 2.0–2.2 (4H, m), 2.4–2.6 (4H, m), 2.9–3.0 (2H, m), 3.29 (2H, t, J=7 Hz), 4.47 (2H, s), 7.2–8.1 (9H, s).

Fumarate (desired compound)

$^1$H-NMR (CD$_3$OD) δ: 1.7–1.8 (2H, m), 1.9–2.1 (4H, m), 2.9–3.0 (2H, m), 3.15–3.25 (2H, m), 4.56 (2H, s), 6.63 (2H, s), 7.3–8.0 (9H, m). IR (KBr) cm$^{-1}$: 3400, 1710, 1690, 1580, 1340, 1295, 1170, 910, 750, 570. M.p.: 145°–150° C.

Example 33

2-(3-Chloro-1-phenylpropyl)-2H-1,2-benzothiazin-4(3H) -one 1,1-Dioxide 2-(3-Chloro-1-phenylpropyl)-2H-1,2-benzothiazin-4(3H) -one 1,1-dioxide ethylene ketal (500 mg, 27 mmol.) which was obtained essentially in the same manner as in Example 1-(1) was suspended in a mixture of ethanol (3 mL) and concentrated hydrochloric acid (1 mL), and heated to reflux for 2 hours. The reaction liquid was placed under reduced pressure to distill ethanol off, and extracted with ethyl acetate after addition of water. The ethyl acetate portion was washed with an aqueous saturated sodium chloride solution, dried over anhydrous sodium sulfate, and placed under reduced pressure to distill the solvent off. There was obtained the desired compound (380 mg, 85.6%) as an orange oil.

$^1$H-NMR (CDCl$_3$: 400 MHz) δ: 2.3–2.4 (1H, m), 2.5–2.6 (1H, m), 3.5–3.7 (2H, m), 4.13 (1H, d, J=19 Hz), 4.60 (1H, d, J=19 Hz), 5.4–5.5 (1H, m), 6.9–7.8 (9H, m).

Example 34

2-[3-(4-Cyano-4-phenylpiperidino)-1-phenylpropyl]-2H-1,2-benzothiazin-4(3H)-one 1,1-Dioxide Fumarate 4-Cyano-4-phenylpiperidine (236 mg, 1.06 mmol.) was dissolved in water (3 mL), made alkaline by an aqueous saturated sodium hydrogen carbonate solution, and extracted with dichloromethane. The dichloromethane portion was dried over anhydrous sodium sulfate, and placed under reduced pressure to distill the solvent off, to give an oil. The oil and 2-(3-chloro-1-phenylpropyl)-2H- 1,2-benzothiazin-4(3H)-one 1,1-dioxide obtained in Example 33 were treated essentially in the same manner as in Example 31, to give a free base of the desired compound (160 mg, 30.2%) and its fumarate (37 mg, 18.8%, orange solid).

Free base $^1$H-NMR (CDCl$_3$, 400 MHz) δ: 2.0–2.2 (6H, m), 2.5–2.6 (4H, m), 2.9–3.1 (2H, m), 4.18 (1H, d, J=19 Hz), 4.58 (1H, d, J=19 Hz), 5.3–5.4 (1H, m), 6.9–7.8 (9H, m).

Fumarate (desired compound)

$^1$H-NMR (CDCl$_3$, 400 MHz) δ: 2.1–2.3 (6H, m), 2.5–2.6 (4H, m), 2.9–3.1 (2H, m), 3.40 (1H, s), 4.20 (1H, s), 5.3–5.4 (1H, m), 7.0–7.8 (9H, m). IR (KBr) cm$^{-1}$: 3400, 1690, 1590, 1450, 1335, 1280, 1230, 1170, 1080, 980, 765, 700, 640, 590, 550. M.p.: 188°–190° C.

Example I

2-[1-Phenyl-3-(1-pyrrolidinyl)]propyl-1,2-benzisothiazol-3(2H)-one 1,1-Dioxide Fumarate (1) 2-[1-Phenyl-3-(1-pyrrolidinyl)]propyl-1,2-benzisothiazol-3(2H)-one 1,1-Dioxide In dimethylformamide (DMF) (8 mL) were suspended 1-[(3-chloro-3-phenyl)propyl]pyrrolidine hydrochloride (1.04 g, 4.00 mmol.), anhydrous potassium carbonate (1.11 g, 8.03 mmol.), and saccharin (733 mg, 4.00 mmol). The suspension was heated under stirring to 100° C. for 3 hours to carry out a reaction. The reaction liquid was cooled to room temperature, and placed under reduced pressure to distill DMF off. To the residue were added water and ethyl acetate, and the organic layer was taken out. The organic portion was washed with an aqueous saturated sodium chloride solution, dried over anhydrous sodium sulfate, and placed under reduced pressure to distill the solvent off. The residue was subjected to silica gel column chromatography (chloroform/methanol=30/1) to obtain 438 mg of the desired compound (yield 30%) as a pale yellow oil.

IR (KBr) cm$^{-1}$: 2950, 2780, 1720, 1455, 1330, 1290, 1250, 1180, 750, 695, 670. $^1$H-NMR (CDCl$_3$) δ: 1.4–1.2 (4H, m), 2.2–3.1 (8H, m), 5.39 (1H, t, J=7 Hz), 7.1–8.0 (9H, m).

(2) 2-[1-Phenyl-3-(1-pyrrolidinyl)]propyl-1,2-benzisothiazol-3(2H)-one 1,1-Dioxide Fumarate A solution of fumaric acid (128 mg, 1.10 mmol.) in hot ethanol (4 mL) was added to a solution of 2-[1-phenyl-3-(1-pyrrolidinyl)]propyl-1,2-benzisothiazol-3(2H)-one 1,1-dioxide (408 mg, 1.10 mmol). The obtained solution was placed under reduced pressure to distill the solvent off. The residue was recrystallized from ethanol/ether, to give 360 mg of the desired compound (yield 67%) as a white crystalline product.

IR (KBr) cm$^{-1}$: 2910, 2640, 2600, 2560, 2470, 1675, 1595, 1465, 1445, 1380, 1330, 1310, 1220, 960, 750, 690. $^1$H-NMR (CDCl$_3$/CD$_3$OD=6/1) δ: 2.92 (6H, s), 3.3–3.8 (4H, m), 7.2–7.7, 7.8–8.1 (5H, m).

Example II 2-(1-Phenyl-3-thiomorpholino)propyl-1,2-benzisothiazol-3(2H)-one 1,1-Dioxide Fumarate (1) 1-Bromo-3-chloro-1-phenylpropane 3-Chloro-1-phenylpropane (3.09 g, 20 mmol.), N-bromosuccinimide (3.56 g, 20 mmol.), benzoyl peroxide (catalytic amount), and carbon tetrachloride (30 mL) were mixed, and the resulting mixture was heated to reflux for 15 min while it was exposed to a light of 100V/100 W, to perform a reaction. Insolubles were filtered off. The reaction liquid was washed with an aqueous saturated sodium hydrogen carbonate solution and an aqueous saturated sodium chloride solution, dried over anhydrous sodium sulfate, and placed under reduced pressure to distill the solvent off, to give 4.58 g of the desired compound (yield 98%) as an oil.

$^1$H-NMR (CDCl$_3$) δ: 2.1–2.9 (2H, m), 3.3–3.9 (2H, m), 5.16 (1H, dd, J=7 Hz, 10 Hz), 7.1–7.5 (5H, m).

(2) 2-(3-Chloro-1-phenyl)propyl-1,2-benzisothiazol-3(2H)-one 1,1-Dioxide

In DMF (10 mL) were suspended 1-bromo-3-chloro-1-phenylpropane (1.00 g, 4.28 mmol.), saccharin (780 mg, 4.3 mmol), and potassium carbonate (600 mg, 4.4 mmol.). The suspension was heated under stirring to 100° C. for 3 min. to carry out a reaction. The reaction liquid was placed under reduced pressure to distill DMF off. To the residue were added water and ethyl acetate, and the organic layer was taken out. The organic portion was washed with water and an aqueous saturated sodium chloride solution, dried over anhydrous sodium sulfate, and placed under reduced pressure to distill the solvent off. The residue was subjected to silica gel column chromatography (hexane/ethyl acetate=2/1) to obtain 440 mg of the desired compound (yield 31%) as an oil.

IR (KBr) cm$^{-1}$: 1720, 1590, 1450, 1390, 1325, 1290, 1250, 1180, 1125, 1060, 1010, 940, 850, 760, 750, 695, 670, 580, 560, 535, 510. $^1$H-NMR (CDCl$_3$) δ: 2.5–3.2 (2H, m), 3.3–3.8 (2H, m), 5.46 (1H, t, J=8 Hz), 7.1–8.0 (9H, m).

(3) 2-(1-Phenyl-3-thiomorpholino)propyl-1,2-benzisothiazol-3(2H)-one 1,1-Dioxide 2-(3-Chloro-1-phenyl)propyl-1,2-benzisothiazol-3(2H)-one 1,1-dioxide (1.01 g, 3 mmol.) and thiomorpholine (0.62 g, 6 mmol.) were mixed with each other. The mixture was heated to 110° C. under stirring for 6 hours, to perform a reaction. The reaction liquid was cooled to room temperature. To the cooled liquid were added 2N-hydrochloric acid and ethyl acetate, and the aqueous layer was taken out. The aqueous portion was made alkaline by addition of an aqueous saturated sodium hydrogen carbonate solution. An oil precipitated, which was then extracted with ethyl acetate. The ethyl acetate portion was washed with an aqueous saturated sodium chloride solution, dried over anhydrous sodium sulfate, and placed under reduced pressure to distill the solvent off. The residue was subjected to silica gel column chromatography (hexane/ethyl acetate=2/1) to obtain 420 mg of the desired compound (yield 35%) as a colorless oil.

IR (KBr) cm$^{-1}$: 2800, 1720, 1450, 1330, 1285, 1255, 1180, 1130, 750, 700, 580. $^1$H-NMR (CDCl$_3$) δ: 2.3–2.9 (12H, m), 5.3–5.4 (1H, m), 7.2–7.4 (3H, m), 7.6–7.7 (2H, m), 7.7–7.8 (2H, m), 7.84 (1H, dd, J=1 Hz, 8 Hz), 7.94 (1H, dd, J=1 Hz, 7 Hz).

(4) 2-(1-Phenyl-3-thiomorpholino)propyl-1,2-benzisothiazol-3(2H)-one 1,1-Dioxide Fumarate A solution of fumaric acid (120 mg, 1 mmol.) in hot ethanol (12 mL) was added to a solution of 2-(1-phenyl-3-thiomorpholino)propyl-1,2-benzisothiazol-3(2H)-one 1,1-dioxide (400 mg, 1 mmol.) in ethanol (20 mL). The mixture was stirred at room temperature. Insolubles precipitated and were collected by filtration and recrystallized from water, to give 325 mg of the desired compound (yield 64%) as a white crytalline powder.

M.p.: 187°–189° C., IR (KBr) cm$^{-1}$: 1720, 1335, 1290, 1250, 1175. $^1$H-NMR (D$_2$O) δ: 2.8–4.0 (12H, m), 5.4–5.6 (1H, m), 6.61 (2H, s), 7.4–7.5 (3H, m), 7.6–7.7 (2H, m), 7.9–8.1 (4H, m).

In the following Examples III to XX, the compounds were prepared essentially in the same manner as in Example I. The prepared compounds and characteristics thereof are set forth below.

Example III 2-(2-Morpholino-1-phenyl)ethyl-1,2-benzisothiazol-3(2H)-one 1,1-Dioxide Mesylate M.p.: 240°–241° C. (decomp.), IR (KBr) cm$^{-1}$: 1745, 1325, 1290, 1260, 1220, 1180, 1160, 1040, 555. $^1$H-NMR (CD$_4$OD) δ: 2.64 (3H, s), 3.2–4.2 (8H, m), 3.97 (1H, dd, J=4 Hz, 14 Hz), 5.91 (1H, dd, J=4 Hz, 12 Hz), 7.3–7.7 (5H, m), 7.9–8.2 (4H, m).

Example IV 2-(4-Morpholino-1-phenyl)butyl-1,2-benzisothiazol-3(2H)-one 1,1-Dioxide Fumarate M.p.: 175°–177° C. (decomp.), IR (KBr) cm$^{-1}$: 3450, 1720, 1635, 1330, 1290, 1255, 1180. $^1$H-NMR (CD$_3$OD) δ:

1.8–2.0 (1H, m), 2.3–2.5 (1H, m), 2.6–2.8 (1H, m), 3.0–4.2 (10H, m), 5.45 (1H, dd, J=7 Hz, 9 Hz), 6.64 (2H, s), 7.4–7.5 (3H, m), 7.6–7.7 (2H, m), 7.9–8.0 (2H, m), 8.04 (1H, d, J=8 Hz), 8.07 (1H, d, J=8 Hz).

Example V 2-(1-Phenyl-3-piperidino)propyl-1,2-benzisothiazol-3(2H)-one 1,1-Dioxide Fumarate M.p. 182° C., IR (KBr) cm$^{-1}$: 3440, 2940, 1730, 1595, 1445, 1390, 1325, 1295, 1255, 1195, 985, 750, 700, 675. $^1$H-NMR (DMSO-d$_6$) δ: 1.2–1.7 (6H, m), 2.2–3.0 (8H, m), 5.36 (1H, t, J=8 Hz), 6.55 (2H, s), 7.3–8.2 (9H, m), 10.0 (2H, brs).

Example VI

2-[3-(Perhydroazepin-1-yl)-1-phenyl]propyl-1,2-benzisothiazol-3(2H)-one 1,1-Dioxide Fumarate IR (KBr) cm$^{-1}$: 3410, 2920, 2620, 1720, 1320, 1285, 1250, 1180, 975, 740. $^1$H-NMR (CD$_3$OD) δ: 1.5–2.1 (8H, s), 2.4–3.5 (8H, m), 5.1–5.5 (1H, m), 6.67 (2H, s), 7.1–8.1 (9H, m).

Example VII 2-(3-(4-methylpiperidino)-1-phenyl]propyl-1,2-benzisothiazol-3(2H)-one 1,1-Dioxide Fumarate M.p.: 177°–178° C., IR (KBr) cm$^{-1}$: 3400, 3000, 2950, 2750, 2550, 1720, 1695, 1630, 1590, 1530, 1450, 1390, 1330, 1290, 1250, 1200, 1180, 1050, 1000, 985, 970, 950, 920, 790, 750, 695, 670, 630, 580, 550, 505. $^1$H-NMR (CD$_3$OD) δ: 1.00 (3H, d, J=6 Hz), 1.0–2.0 (5H, m), 2.5–3.7 (8H, m), 5.2–5.4 (1H, m), 7.2–8.1 (9H, m).

Example VIII

2-[3-(4-Carbamoylpiperidino)-phenyl]propyl-1,2-benzisothiazol-3(2H)-one 1,1-Dioxide Fumarate M.p.: 178°–180° C., IR (KBr) cm$^{-1}$: 3420, 1725, 1670, 1610, 1325, 1290, 1265, 1180, 980, 750, 640, 580. $^1$H-NMR (D$_2$O) δ: 1.8–2.2, 2.6–3.8 (13H, m), 5.50 (1H, dd, J=7 Hz, 9 Hz), 6.67 (2H, s), 7.4–7.5 (3H, m), 7.6–7.7 (2H, m), 7.9–8.1 (4H, m).

Example IX 2-(3-Morpholino-1-pheny)propyl-1,2-benzisothiazol-3(2H)-one 1,1-Dioxide Fumarate M.p.: 159° C., IR (KBr) cm$^{-1}$: 3425, 2855, 1720, 1655, 1610, 1495, 1450, 1370, 1330, 1290, 1270, 1250, 1180, 1130, 1095, 1060, 980, 900, 870, 790, 750, 690, 675, 640, 610, 580, 550, 510. $^1$H-NMR (CD$_3$OD) δ: 2.4–3.0 (8H, m), 3.6–3.8 (4H, m), 5.2–5.4 (1H, m), 6.66 (2H, s), 7.2–8.1 (9H, m).

Example X

2-[3-(4-Ethyl-1-piperazinyl)-1-pheny]propyl-1,2-benzisothiazol-3(2H)-one 1,1-Dioxide Difumarate M.p.: above 200° C. (decomp.), IR (KBr) cm$^{-1}$: 3400, 1720, 1320, 1290, 1250, 1180, 980, 750, 640. $^1$H-NMR (CD$_3$OD) δ: 1.28 (3H, t), 2.4–3.2 (14H, m), 5.2–5.4 (1H, m), 6.66 (4H, s), 7.3–8.1 (9H, m).

Example XI

2-[3-(4-Acetyl-1-piperazinyl)-1-pheny]propyl-1,2-benzisothiazol-3(2H)-one 1,1-Dioxide Fumarate M.p.: 129°–130° C., IR (KBr) cm$^{-1}$: 3400, 3000, 2950, 2575, 1720, 1640, 1410, 1325, 1290, 1250, 1180, 980, 750, 670, 640, 580, 500. $^1$H-NMR (CD$_3$OD) δ: 2.04 (3H, s), 2.4–2.9 (8H, m), 3.4–3.7 (4H, m), 5.2–5.5 (1H, m), 6.68 (2H, s), 7.2–8.1 (9H, m).

Example XII

2-[1-Phenyl-3-[4-(2-pyrimidinyl)-1-piperazinyl] propyl-1,2-benzisothiazol-3(2H)-one 1,1-Dioxide Hydrochloride IR (KBr) cm$^{-1}$: 3470, 1725, 1620, 1580, 1550, 1440, 1330, 1290, 1250, 1180, 580. $^1$H-NMR (D$_2$O) δ: 2.8–4.0 (12H, m), 5.55 (1H, dd, J=7 Hz, 9 Hz), 6.87 (1H, t, J=5 Hz), 7.4–7.5 (3H, m), 7.6–7.7 (2H, m), 7.9–8.1 (4H, m), 8.44 (2H, d, J=5 Hz).

Example XIII

2-[1-(4-Chlorophenyl)-3-piperidino]propyl-1,2-benzisothiazol-3(2H)-one 1,1-Dioxide Fumarate M.p.: 193°–194° C. (decomp.), IR (KBr) cm$^{-1}$: 3400, 2945, 1720, 1650, 1590, 1485, 1455, 1330, 1280, 1240, 1175, 1120, 1085, 1055, 1005, 980, 830, 780, 745, 720, 645, 630, 600, 575, 550, 520, 505. $^1$H-NMR (CD$_3$OD) δ: 1.4–2.0 (6H, m), 3.0–3.3 (8H, m), 5.2–5.4 (1H, m), 6.62 (2H, s), 7.2–8.1 (8H, m).

Example XIV

2-[1-(4-chlorophenyl)-3-morpholino]propyl-1,2-benzisothiazol-3(2H)-one 1,1-Dioxide Fumarate M.p.: 189°–190° C., IR (KBr) cm$^{-1}$: 3425, 1725, 1610, 1590, 1490, 1450, 1400, 1325, 1280, 1250, 1170, 1125, 1090, 1060, 1010, 975, 920, 870, 840, 800, 780, 740, 715, 670, 640, 615, 580, 570, 505. $^1$H-NMR (CD$_3$OD) δ: 2.3–3.0 (8H, m), 3.5–3.8 (4H, m), 5.2–5.4 (1H, m), 6.66 (2H, s), 7.2–7.7 (4H, m), 7.8–8.1 (5H, m).

Example XV

2-[1-(4-Methoxyphenyl)-3-piperidino]propyl-1,2-benzisothiazol-3(2H)-one 1,1-Dioxide Fumarate M.p.: 173°–176° C. (decomp.), IR (KBr) cm$^{-1}$: 3410, 2950, 2510, 1735, 1610, 1510, 1325, 1290, 1245, 1180, 980, 745. $^1$H-NMR (CD$_3$OD) δ: 1.4–2.1 (6H, m), 2.4–3.4 (8H, m), 3.79 (3H, s), 5.0–5.4 (1H, m), 6.73 (2H, s), 6.7–7.0, 7.3–8.1 (8H, m).

Example XVI

6-Chloro-2-(4-phenyl-3-piperidino)propyl-1,2-benzisothiazol-3(2H)-one 1,1-Dioxide Fumarate M.p.: 212°–214° C. (decomp.), IR (KBr) cm$^{-1}$: 3400, 2940, 1730, 1585, 1320, 1260, 1240, 1175, 980. $^1$H-NMR (DMSO-d$_6$) δ: 1.1–1.6 (6H, m), 2.0–2.9 (8H, m), 5.33 (H, t, J=7 Hz), 6.57 (2H, s), 7.1–7.6 (5H, m), 7.9–8.0 (2H, m), 8.3–8.4 (40, m).

Example XVII

6-Chloro-2-(3-morpholino-1-phenyl)propyl-1,2-benzisothiazol-3(2H)-one 1,1-Dioxide Fumarate M.p.: 197°–198° C., IR (KBr) cm$^{-1}$: 3425, 1725, 1585, 1490, 1450, 1400, 1390, 1320, 1260, 1240, 1170, 1125, 1090, 975, 865, 830, 800, 750, 690, 655, 630, 580, 520, 450. $^1$H-NMR (CD$_3$OD) δ: 2.3–3.0 (8H, m), 3.5–3.8 (4H, m), 5.2–5.4 (4H, m), 6.66 (2H, s), 7.2–7.7 (5H, m), 7.9–8.2 (3H, m).

Example XVIII

6-Methoxy-2-(1-phenyl-3-piperidino)propyl-1,2-benzisothiazol-3(2H)-one 1,1-Dioxide Fumarate M.p.: 199°–201° C. (decomp.), IR (KBr) cm$^{-1}$: 3420, 2950, 1725, 1600, 1580, 1490, 1320, 1265, 1170, 980. $^1$H-NMR (DMSO-d$_6$) δ: 1.1–1.7 (6H, m), 2.0–2.9 (8H, m), 3.96 (3H, s), 5.32 (1H, t, J=7 Hz), 6.57 (2H, s), 7.2–8.0 (8H, m).

Example XIX

6-Methoxy-2-(3-morpholino-1-phenyl)propyl-1,2-benzisothiazol-3(2H)-one 1,1-Dioxide Fumarate M.p.: 196°–198° C. (decomp.), IR (KBr) cm$^{-1}$: 1725, 1605, 1580, 1490, 1320, 1270, 1170. $^1$H-NMR (D$_2$O) δ: 2.7–4.3 (12H, m), 3.97 (3H, s), 5.50 (1H, dd, J=6 Hz, 9 Hz), 6.59 (2H, s), 7.4–7.5 (4H, m), 7.6–7.7 (3H, m), 7.94 (1H, d, J=1 Hz).

Example XX

4-Chloro-2-(3-piperidino-1-phenyl)propyl-1,2-benzisothiazol-3(2H)-one 1,1-Dioxide Fumarate M.p.: 208° C., IR (KBr) cm$^{-1}$: 3425, 3050, 2950, 2675, 2525, 1720, 1570, 1445, 1395, 1340, 1250, 1210, 1180, 1150, 980, 930, 790, 760, 690, 660, 635, 580, 560, 520, 470. $^1$H-NMR (CD$_3$OD) δ: 1.3–2.1 (6H, m), 2.5–3.4 (8H, m), 5.2–5.5 (1H, m), 6.64 (2H, s), 7.2–8.0 (3H, m).

In the following Examples XXI to XXVIII, the compounds were prepared essentially in the same manner as in Example II. The prepared compounds and characteristics thereof are set forth below.

Example XXI 2-(1-Phenyl-3-thiomorpholino)propyl-1,2-benzisothiazol-3(2H)-one 1,1,S-trioxide Fumarate M.p.: 178°–180° C. (decomp.), IR (KBr) cm$^{-1}$: 3420, 1735, 1395, 1320, 1290, 1250, 1180, 1020, 1000, 980, 925, 760, 740, 640, 580. $^1$H-NMR (D$_2$O) δ: 2.8–3.0 (1H, m), 3.0–3.4 (7H, m), 3.6–3.9 (4H, m), 5.51 (1H, t, J=8 Hz), 6.66 (2H, s), 7.4–7.5 (3H, m), 7.6–7.7 (2H, m), 7.8–8.0 (3H, m), 8.02 (1H, d, J=7 Hz).

Example XXII 2-(1-Phenyl-3-thiomorpholino)propyl-1,2-benzisothiazol-3(2H)-one 1,1,S,S-tetraoxide Mesylate Amorphous IR (KBr) cm$^{-1}$: 3420, 1720, 1320, 1290, 1250, 1180, 1130. $^1$H-NMR (D$_2$O) δ: 2.8–3.2 (2H, m), 2.82 (3H, s), 3.4–3.6 (2H, m), 3.6–3.8 (4H, m), 3.8–4.1 (4H, m), 5.52 (1H, dd, 7=7 Hz, 9 Hz), 7.4–7.6 (3H, m), 7.6–7.7 (2H, m), 7.8–8.1 (4H, m).

Example XXIII

2-[3-(2-Methylthiomorpholino)-1-phenyl]propyl-1,2-benzisothiazol-3(2H)-one 1,1-Dioxide Fumarate M.p.: 170°–178° C., IR (KBr) cm$^{-1}$: 3400, 1730, 1330, 1290, 1250, 1180, 970, 750. $^1$H-NMR (CDCl$_3$) δ: 1.12, 1.16 (3H, d, J=8 Hz), 2.2–3.2 (11H, m), 5.2–5.4 (1H, m), 6.72 (2H, s), 7.2–8.0 (9H, m).

Example XXIV

2-[3-(3-Methylthiomorpholino)-1-phenyl]propyl-1,2-benzisothiazol-3(2H)-one 1,1-Dioxide Fumarate M.p.: 175°–177° C., IR (KBr) cm$^{-1}$: 3400, 1730, 1450, 1380, 1330, 1290, 1250, 1180, 970, 750, 690, 670, 640, 580, 540, 510. $^1$H-NMR (CD$_3$OD) δ: 1.1–1.3 (3H, m), 2.3–3.7 (11H, m), 5.2–5.4 (1H, m), 6.68 (2H, s), 7.2–8.1 (9H, m).

Example XXV

2-[3-(2,2-Dimethylthiomorpholino)-1-phenyl]propyl-1,2-benzisothiazol-3(2H)-one 1,1-Dioxide Mesylate Amorphous IR (KBr) cm$^{-1}$: 3400, 1730, 1330, 1290, 1240, 1180, 1060, 785, 560, 540. $^1$H-NMR (D$_2$O) δ: 1.35 (3H, s), 1.55 (3H, s), 2.8–3.4 (8H, m), 2.84 (3H, s), 3.5–3.6 (1H, m), 3.8–3.9 (1H, m), 5.4–5.6 (1H, m), 7.4–7.5 (3H, m), 7.6–7.7 (2H, m), 7.8–8.1 (4H, m).

Example XXVI

2-[3-(2,6-Dimethylthiomorpholino)-1-phenyl]propyl-1,2-benzisothiazol-3(2H)-one 1,1-Dioxide Fumarate M.p.: 167° C., IR (KBr) cm$^{-1}$: 3400, 1730, 1690, 1555, 1445, 1380, 1320, 1280, 1250, 1180, 1050, 980, 750, 695, 670, 640, 580, 510. $^1$H-NMR (CD$_3$OD) δ: 1.12 (3H, dd, J=4 Hz, 8 Hz), 1.30 (3H, dd, J=4 Hz, 8 Hz), 2.2–3.4 (8H, m), 5.2–5.5 (1H, m), 6.66 (2H, s), 7.2–8.1 (9H, m).

Example XXVII

2-[1-Phenyl-3-(2-phenylthiomorpholino)]propyl-1,2-benzisothiazol-3(2H)-one 1,1-Dioxide Mesylate Amorphous IR (KBr) cm$^{-1}$: 3420, 1720, 1450, 1330, 1290, 1250, 1180, 1060, 1035, 750, 695, 580. $^1$H-NMR (CD$_3$OD) δ: 2.71 (3H, s), 2.6–3.1 (2H, m), 3.2–3.7 (6H, m), 3.8–4.0 (2H, m), 4.3–4.4 (1H, m), 5.3–5.4 (1H, m), 7.3–7.7 (1OH, m), 7.9–8.1 (4H, m).

Example XXVIII

2-[1-(4-Fluorophenyl)-3-thiomorpholino]propyl-1,2-benzisothiazol-3(2H)-one 1,1-Dioxide Fumarate M.p.: 186°–187° C., IR (KBr) cm$^{-1}$: 3400, 1720, 1710, 1600, 1505, 1460, 1330, 1300, 1250, 1220, 1180, 1160, 920, 840, 780, 750, 670, 630, 580, 510. $^1$H-NMR (CD$_3$OD) δ: 2.5–2.6 (2H, m), 2.7–3.2 (1OH, m), 5.37 (1H, dd, J=6 Hz, 9 Hz), 6.72 (2H, s), 7.1–8.1 (8H, m).

In the following Examples XXIX to XXXI, the compounds were prepared essentially in the same manner as in Example I. The prepared compounds and characteristics thereof are set forth below.

Example XXIX 2-(3-Dimethylamino-1-phenyl)propyl-1,2-benzisothiazol-3(2H)-one 1,1-Dioxide Fumarate M.p.: 170°–173° C., IR (KBr) cm$^{-1}$: 3410, 2940, 2660, 1720, 1680, 1610, 1455, 1325, 1290, 1250, 1180, 980, 745, 640, 580. $^1$H-NMR (CD$_3$OD) δ: 2.86 (6H, s), 2.4–3.4 (4H, m), 5.2–5.5 (1H, m), 6.68 (2H, s), 7.1–8.1 (9H, m).

Example XXX 2-(3-Diethylamino-1-phenyl)propyl-1,2-benzisothiazol-3(2H)-one 1,1-Dioxide Fumarate M.p.: 173°–176° C., IR (KBr) cm$^{-1}$: 3430, 1730, 1330, 1295, 1260, 1185, 990. $^{1}$H-NMR (D$_2$O) δ: 1.27 (6H, t, J=7 Hz), 2.6–3.4 (4H, m), 3.26 (4H, q, J=7 Hz), 5.50 (1H, t, J=8 Hz), 6.65 (2H, s), 7.4–8.1 (9H, m).

Example XXXI 2-(3-Benzylethylamino-1-phenyl)propyl-1,2-benzisothiazol-3(2H)-one 1,1-Dioxide Fumarate Amorphous IR (KBr) cm$^{-1}$: 3400, 1720, 1450, 1370, 1330, 1285, 1245, 1180, 970, 740, 690, 580. $^{1}$H-NMR (CD$_3$OD) δ: 1.31 (3H, t, J=8 Hz), 2.5–3.3 (6H, m), 4.28 (2H, s), 5.1–5.4 (1H, m), 6.70 (2H, s), 7.2–7.6 (12H, m, ArH), 7.8–8.1 (2H, m).

Example XXXII 2-(3-Morpholino-1-phenyl)propyl-1,2-benzisothiazol-3(2H)-one 1-Oxide Fumarate (1) 2-(3-Morpholino-1-phenyl)propyl-1,2-benzisothiazol-3(2H)-one 1-Oxide In DMF (2 mL) were suspended 4-[(3-chloro-3-phenyl)propyl]morpholine hydrochloride (116 mg, 0.42 mmol.), 1,2-benzisothiazol-3(2H)-one 1-oxide (70 mg, 0.42 mmol.), and cesium carbonate (137 mg, 0.42 mmol.). The suspension was stirred at room temperature for 70 hours to carry out a reaction. The reaction liquid was placed under reduced pressure to distill DMF off. To the residue were added water and ethyl acetate, and the organic layer was taken out. The organic portion was washed with an aqueous saturated sodium chloride solution, dried over anhydrous sodium sulfate, and placed under reduced pressure to distill the solvent off. The residue was subjected to silica gel column chromatography (chloroform/methanol=100/1) to obtain 19 mg of the desired compound (yield 12%) as a colorless oil.

$^{1}$H-NMR (CDCl$_3$) δ: 2.3–2.8 (8H, m), 3.6–3.8 (4H, m), 5.76 (1H, t, J=8 Hz), 7.3–7.4 (3H, m), 7.5–7.6 (2H, m), 7.7–7.8 (3H, m), 7.97 (1H, dd, J=7 Hz, 1 Hz).

(2) 2-(3-Morpholino-1-phenyl)propyl-1,2-benzisothiazol-3(2H)-one 1-Oxide Fumarate A solution of fumaric acid (6 mg) in hot ethanol (6 mL) was added to a solution of 2-(3-morpholino-1-phenyl)propyl-1,2-benzisothiazol-3(2H)-one 1-oxide (19 mg) in ethanol (2 mL). The mixture was concentrated under reduced pressure to approx. 1 mL, and then allowed to stand two days at room temperature. Insolubles precipitated and were collected by filtration. The collected insolubles were washed successively with ethanol and hexane, to give 15 mg of the desired compound (yield 61%) as a white crystalline product.

IR (KBr) cm$^{-1}$: 3420, 1700, 1620, 1460, 1300, 1240, 1120. $^{1}$H-NMR (D$_2$O) δ: 2.7–4.2 (12H, m), 5.72 (1H, t, J=8 Hz), 6.65 (2H, s), 7.4–7.6 (5H, m), 7.8–8.0 (3H, m), 8.04 (1H, d, J=7 Hz).

Example XXXIII 2-(3-Piperidino-1-phenyl)propyl-1,2-benzisothiazoline 1,1-Dioxide Fumarate (1) 2-(3-Piperidino-1-phenyl)propyl-1,2-benzisothiazoline 1,1-Dioxide In anhydrous ethanol was dissolved sodium (131 mg, 5.7 mmol.). To the obtained solution were added 1,2-benzisothiazoline (483 mg, 2.85 mmol.) and 1-((3-chloro-3-phenyl)propyl]piperidine hydrochloride (783 mg, 2.85 mmol). The mixture was then heated for 7 hours under refluxing. The reaction liquid was placed under reduced pressure to distill the solvent off. To the residue were added water and ethyl acetate, and the organic layer was taken out. The organic portion was washed with an aqueous saturated sodium chloride solution, dried over anhydrous sodium sulfate, and placed under reduced pressure. The residue was subjected to silica gel column chromatography (chloroform/methanol=40/1) to give 890 mg of the desired compound (yield 84%) as a white crystalline product.

M.p.: 117°–118° C., IR (KBr) cm$^{-1}$: 2920, 2800, 1450, 1280, 1210, 1170, 1150, 1120, 1060, 1040, 800, 760, 745, 720, 700, 560. $^{1}$H-NMR (CDCl$_3$) δ: 1.0–1.8 (6H, m), 1.9–2.6 (8H, m), 3.95 (1H, d, J=14 Hz), 4.30 (1H, d, J=14 Hz), 4.95 (1H, t, J=7 Hz), 7.1–7.9 (9H, m).

(2) 2-(3-Piperidino-1-phenyl)propyl-1,2-benzisothiazoline 1,1-Dioxide Fumarate

A solution of fumaric acid (130 mg, 1.12 mmol.) in hot ethanol (13 mL) was added to a solution of 2-(3-piperidino-1-phenyl)propyl-1,2-benzisothiazoline 1,1-dioxide (415 mg, 1.12 mmol.) in ethanol (20 mL). The mixture was allowed to stand ovenight at room temperature. Insolubles precipitated and were collected by filtration. The collected insolubles were washed successively with ethanol and hexane, to give 430 mg of the desired compound (yield 79%) as a white crystalline product.

M.p.: 205°–206° C. (decomp.), IR (KBr) cm$^{-1}$: 3420, 2930, 1720, 1640, 1600, 1450, 1285, 1170, 1160, 1120, 980, 755, 630. $^{1}$H-NMR (DMSO-d$_6$) δ: 1.2–1.8 (6H, m), 2.1–2.9 (8H, m), 4.02 (1H, d, J=14 Hz), 4.50 (1H, d, J=14 Hz), 4.91 (1H, t, J=7 Hz), 6.54 (2H, s), 7.1–7.9 (9H, m).

Example XXXIV 2-(3-Morpholino-1-phenyl)propyl-1,2-benzisothiazoline 1,1-Dioxide Fumarate This was prepared essentially in the same manner as in Example XXXIII.

M.p.: 191°–192° C., IR (KBr) cm$^{-1}$: 3420, 1710, 1450, 1310, 1280, 1170, 1150, 1120, 980, 765, 630. $^{1}$H-NMR (DMSO-d$_6$) δ: 2.0–2.6 (8H, m), 3.3–3.7 (4H, m), 4.02 (1H, d, J=15 Hz), 4.47 (1H, d, J=15 Hz), 4.91 (1H, t, J=7 Hz), 6.61 (2H, s), 7.1–7.9 (9H, m).

INDUSTRIAL APPLICABILITY

The alkylenediamine derivative of the invention and its pharmacologically acceptable salt can relieve urinating contraction which is observed under high intracystic pressure, and can be used for treating nervous dysuria, chronic prostatitis, chronic cystitis, dysuria caused by neurogenic bladder or unstable bladder, incontinence of urine, urgency of micturition, and residual urine, and therefore is of value as an active ingredient of a therapeutic agent for treating dysuria.

We claim:

1. An alkylenediamine derivative having the formula

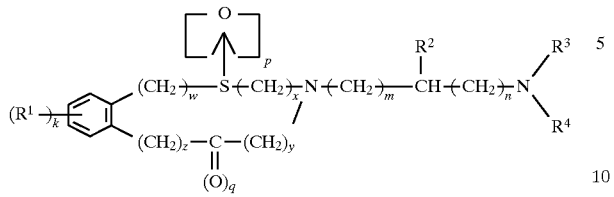

in which

R¹ represents an atom or a group selected from the group consisting of hydrogen, alkyl having 1–8 carbon atoms, halogen, haloalkyl having 1–4 carbon atoms, hydroxyl, alkoxy having 1–8 having 1–8 carbon atoms, aryloxy having 4–10 carbon atoms, aralkyloxy having 5–14 carbon atoms, its alkyl portion having 1–4 carbon atoms, nitro, amino, cyano, alkylamino having 1–8 carbon atoms, aralkylamino having 5–14 carbon atoms, its alkyl portion having 1–4 carbon atoms, arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms, its alkyl portion having 1–4 carbon atoms, aryloxycarbonyl having 5–11 carbon atoms, carbamoyl, sulfo, alkoxysulfonyl having 1–8 carbon atoms, aralkyloxysulfonyl having 5–14 carbon atoms, its alkyl portion having 1–4 carbon atoms, aryloxysulfonyl having 4–10 carbon atoms, sulfonamide, and 1H-tetrazol-5-yl;

R² represents an aryl group having 4–10 carbon atoms, aralkyl group having 5–14 carbon atoms, its alkyl portion having 1–4 carbon atoms, or an aromatic heterocyclic group each of which may have one to five same or different substituents selected from the group consisting of alkyl having 1–8 carbon atoms, halogen, haloalkyl having 1–4 carbon atoms, hydroxyl, alkoxy having 1–8 carbon atoms, aryloxy having 4–10 carbon atoms, aralkyloxy having 5–14 carbon atoms, its alkyl portion having 1–4 carbon atoms, nitro, amino, cyano, alkylamino having 1–8 carbon atoms, aralkylamino having 5–14 carbon atoms, its alkylportion having 1–4 carbon atoms, arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms, its alkyl portion having 1–4 carbon atoms, aryloxycarbonyl having 5–11 carbon atoms, carbamoyl, sulfo, alkoxysulfonyl having 1–8 carbon atoms, aralkyloxysulfonyl having 5–14 carbon atoms, its alkyl portion having 1–4 carbon atoms, aryloxysulfonyl having 4–10 carbon atoms, sulfonamide and 1H-tetrazol-5-yl;

each of R³ and R⁴ independently represents hydrogen, alkyl having 1–8 carbon atoms, aralkyl having 5–14 carbon atoms, its alkyl portion having 1–4 carbon atoms, or aryl having 4–10 carbon atoms, or R³ and R⁴ form in combination with the nitrogen atom to which R³ and R⁴ are attached, a hetero ring which may contain another nitrogen, oxygen or sulfur as the ring-forming atom in addition to the former nitrogen atom and which may have a substituent selected from the group consisting of alkyl having 1–8 carbon atoms which may have one or two aryl having 4–10 carbon atoms as substituent, phenyl, hydroxyl, alkoxy having 1–8 carbon atoms, which may have one or two aryl having 4–10 carbon atoms as substituent, aryloxy having 4–10 carbon atoms, carboxyl and cyano, provided that where R² is phenyl, R³ and R⁴ cannot both be hydrogen;

k is an integer of 1 to 4;

each of m and n independently represents an integer of 0–4, under the condition that the total number of m and n is in the range of 0–4;

p is 0, 1 or 2;

q is 0 or 1; and each of w, x, y and z independently is an integer of 0 to 1, under the condition that the total number of w, x, y and z is 1.

2. The alkylenediamine derivative of claim 1, which is represented by the formula (2):

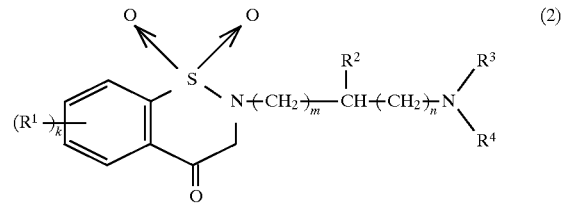

in which R¹, R², R³, R⁴, k, m, and n are the same as those defined in claim 1.

3. The alkylenediamine derivative of claim 1 which is represented by the formula (3):

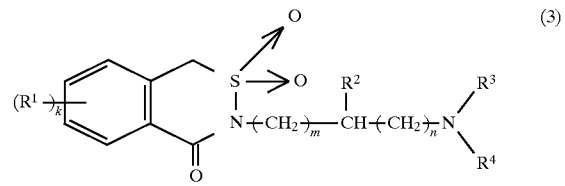

in which R¹, R², R³, R⁴, k, m, and n are the same as those defined in claim 1.

4. A therapeutic agent for treatment of dysuria comprising a carrier and an alkylenediamine derivative having the formula

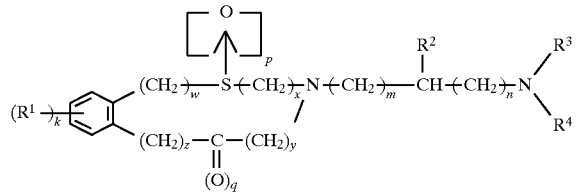

in which

R¹ represents an atom or a group selected from the group consisting of hydrogen, alkyl having 1–8 carbon atoms, halogen, haloalkyl having 1–4 carbon atoms, hydroxyl, alkoxy having 1–8 having 1–8 carbon atoms, aryloxy having 4–10 carbon atoms, aralkyloxy having 5–14 carbon atoms, its alkyl portion having 1–4 carbon atoms, nitro, amino, cyano, alkylamino having 1–8 carbon atoms, aralkylamino having 5–14 carbon atoms, its alkyl portion having 1–4 carbon atoms, arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms, its alkyl portion having 1–4 carbon atoms, aryloxycarbonyl having 5–11 carbon atoms, carbamoyl, sulfo, alkoxysulfonyl having 1–8 carbon atoms, aralkyloxysulfonyl having 5–14 carbon atoms, its alkyl portion having 1–4 carbon atoms, aryloxysulfonyl having 4–10 carbon atoms, sulfonamide, and 1H-tetrazol-5-yl;

$R^2$ represents hydrogen, alkyl having 1–8 carbon atoms, alkenyl having 2–9 carbon atoms, alkoxy having 1–8 carbon atoms, or an aryl having 4–10 carbon atoms, aralkyl having 5–14 carbon atoms, its alkyl portion having 1–4 carbon atoms, or an aromatic heterocyclic group which may have one to five same or different substituents selected from the group consisting of alkyl having 1–8 carbon atoms, halogen, haloalkyl having 1–4 carbon atoms, hydroxyl, alkoxy having 1–8 carbon atoms, aryloxy having 4–10 carbon atoms, aralkyloxy having 5–14 carbon atoms, its alkyl portion having 1–4 carbon atoms, nitro, amino, cyano, alkylamino having 1–8 carbon atoms, aralkylamino having 5–14 carbon atoms, its alkyl portion having 1–4 carbon atoms, arylamino having 4–10 carbon atoms, aliphatic acylamino having 1–8 carbon atoms, carboxyl, alkoxycarbonyl having 2–9 carbon atoms, aralkyloxycarbonyl having 6–15 carbon atoms, its alkyl portion having 1–4 carbon atoms, aryloxycarbonyl having 5–11 carbon atoms, carbamoyl, sulfo, alkoxysulfonyl having 1–8 carbon atoms, aralkyloxysulfonyl having 5–14 carbon atoms, its alkyl portion having 1–4 carbon atoms, aryloxysulfonyl having 4–10 carbon atoms, sulfonamide and 1H-tetrazol-5-yl;

each of $R^3$ and $R^4$ independently represents hydrogen, alkyl having 1–8 carbon atoms, aralkyl having 5–14 carbon atoms, its alkyl portion having 1–4 carbon atoms, or aryl having 4–10 carbon atoms, or $R^3$ and $R^4$ form in combination with the nitrogen atom to which $R^3$ and $R^4$ are attached, a hetero ring which may contain another nitrogen, oxygen or sulfur as the ring-forming atom in addition to the former nitrogen atom and which may have a substituent selected from the group consisting of alkyl having 1–8 carbon atoms which may have one or two aryl having 4–10 carbon atoms as substituent, phenyl, hydroxyl, alkoxy having 1–8 carbon atoms which may have one or two aryl having 4–10 carbon atoms as substituent, aryloxy having 4–10 carbon atoms, carboxyl and cyano, provided that where $R^2$ is hydrogen, $R^3$ and $R^4$ form in combination with the nitrogen atom to which $R^3$ and $R^4$ are attached, a hetero ring which may contain another nitrogen, oxygen or sulfur as the ring-forming atom in addition to the former nitrogen atom and which has a substituent selected from the group consisting of alkyl having 1–8 carbon atoms which may have one or two aryl having 4–10 carbon atoms as substituent, phenyl, hydroxyl, alkoxy having 1–8 carbon atoms which may have one or two aryl having 4–10 carbon atoms, carboxyl and cyano, and where $R^2$ is alkyl or phenyl, $R^3$ and $R^4$ cannot both be hydrogen;

k is an integer of 1 to 4;

each of m and n independently represents an integer of 0 to 4, under the condition that the total number of m and n is in the range of 0 to 4;

p is 0, 1 or 2;

q is 0 or 1; and each of w, x, y and z independently is an integer of 0 to 1, under the condition that the total number of w, x, y and z is 1.

* * * * *